US010780230B2

(12) United States Patent
Fabien et al.

(10) Patent No.: US 10,780,230 B2
(45) Date of Patent: Sep. 22, 2020

(54) AUTO-INJECTOR WITH A DELAY SYSTEM

(71) Applicant: APTAR FRANCE SAS, Le Neubourg (FR)

(72) Inventors: David Fabien, Plouarzel (FR); Thomas Gomez, Saint Aubin de Nedoc (FR); Anthony Saussaye, Louviers (FR); Olivier His, Saint Etienne du Vauvray (FR)

(73) Assignee: APTAR FRANCE SAS, Le Neubourg (FR)

( * ) Notice: Subject to any disclaimer, the term of this patent is extended or adjusted under 35 U.S.C. 154(b) by 468 days.

(21) Appl. No.: 15/578,341

(22) PCT Filed: Jun. 2, 2016

(86) PCT No.: PCT/FR2016/051319
§ 371 (c)(1),
(2) Date: Nov. 30, 2017

(87) PCT Pub. No.: WO2016/193628
PCT Pub. Date: Dec. 8, 2016

(65) Prior Publication Data
US 2018/0154084 A1 Jun. 7, 2018

(30) Foreign Application Priority Data
Jun. 5, 2015 (FR) .................................. 15 55163

(51) Int. Cl.
A61M 5/315 (2006.01)
A61M 5/20 (2006.01)
A61M 5/32 (2006.01)

(52) U.S. Cl.
CPC ............ A61M 5/3157 (2013.01); A61M 5/20 (2013.01); A61M 5/2033 (2013.01);
(Continued)

(58) Field of Classification Search
CPC .......... A61M 5/31511; A61M 5/31538; A61M 5/2033; A61M 5/32; A61M 5/3157;
(Continued)

(56) References Cited

U.S. PATENT DOCUMENTS

2010/0049125 A1* 2/2010 James ................. A61M 5/2033
604/110
2010/0094214 A1* 4/2010 Abry ..................... A61M 5/322
604/110
(Continued)

FOREIGN PATENT DOCUMENTS

| WO | 2011/101380 A1 | 2/2011 |
| WO | 2013/178512 A1 | 12/2013 |
| WO | 2015/073740 A2 | 5/2015 |

OTHER PUBLICATIONS

International Preliminary Report on Patentability with a Translation of Written Opinion issued on Dec. 21, 2017 from the International Bureau in counterpart International Application No. PCT/FR2016/051319.
(Continued)

Primary Examiner — Manuel A Mendez
Assistant Examiner — Tasnim Mehjabin Ahmed
(74) Attorney, Agent, or Firm — Sughrue Mion, PLLC

(57) ABSTRACT

An autoinjector having a body (1) receiving a reservoir (S) containing fluid and a piston (P); a piston rod (5) movable by an injection spring (8) between a primed position and an injection position; and a visual, audible, and/or tactile indicator for indicating the autoinjector may be removed from the injection site. The autoinjector including a retarding system for delaying actuation of the indicator relative to the end of injection, and including a dashpot (16) containing a fluid, a piston (19) in the dashpot, the dashpot or the piston movable in the body during actuation of the retarding system with the other stationary relative to the body, resulting in the
(Continued)

fluid moving out from the dashpot through a flow passage (161; 195) to brake movement.

10 Claims, 23 Drawing Sheets

(52) U.S. Cl.
CPC .... *A61M 5/31511* (2013.01); *A61M 5/31538* (2013.01); *A61M 5/32* (2013.01); *A61M 2005/208* (2013.01); *A61M 2005/2013* (2013.01); *A61M 2005/2086* (2013.01); *A61M 2205/581* (2013.01); *A61M 2205/582* (2013.01); *A61M 2205/583* (2013.01)

(58) Field of Classification Search
CPC .... A61M 2005/2086; A61M 2005/208; A61M 2205/581; A61M 2205/582; A61M 2205/583

See application file for complete search history.

(56) References Cited

U.S. PATENT DOCUMENTS

2013/0218093 A1    8/2013  Markussen et al.
2018/0161507 A1*   6/2018  Fabien ................. A61M 5/326

OTHER PUBLICATIONS

International Search Report for PCT/FR2016/051319 dated Sep. 19, 2016 [PCT/ISA/210].
Written Opinion for PCT/FR2016/051319 dated Sep. 19, 2016 [PCT/ISA/237].

* cited by examiner

US 10,780,230 B2

AUTO-INJECTOR WITH A DELAY SYSTEM

CROSS REFERENCE TO RELATED APPLICATIONS

This application is a National Stage of International Application No. PCT/FR2016/051319 filed Jun. 2, 2016, claiming priority based on French Patent Application No. 1555163 filed Jun. 5, 2016, the contents of all of which are incorporated herein by reference in their entirety.

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they present a certain number of drawbacks.

Thus, in particular when the volume of fluid is relatively large and/or when the injected fluid is relatively viscous, it is desirable to enable the fluid to diffuse from the injection site for a few seconds after said injection. When the user removes the autoinjector immediately after the end of injection, a fraction of the fluid may escape from the user's body, and this reduces the effectiveness of the treatment. It is thus desirable to make provision for the user to continue to hold the autoinjector against the body for a few seconds after the end of injection. This aspect is generally resolved in existing autoinjectors by the operating instructions that ask the user to count silently a certain number of seconds prior to removing the device. This is unreliable and thus unsatisfactory, since the system depends on the user who, in some circumstances, may be disturbed or weakened by the injection action that has just been performed.

Documents WO 2013/178512, WO 2015/073740, WO 2011/101380, and US 2013/218093 describe prior-art autoinjectors.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable in use, that enables the user to determine when the autoinjector must be removed or may be removed from the body after use, that is safe and that prevents any risk of injury, and that is simple and inexpensive to manufacture and to assemble.

The present invention thus provides an autoinjector comprising:
  a body receiving a reservoir, said reservoir containing fluid and including a piston, such as a pre-filled syringe;
  a piston rod that is suitable for co-operating with the piston of said reservoir, said piston rod being movable by an injection spring between a primed position and an injection position in which said piston rod has moved the piston of the reservoir so as to inject the fluid into an injection site; and
  a visual, audible, and/or tactile indicator device for indicating to the user that said autoinjector may be removed from said injection site;
  said autoinjector including a retarding system for delaying the actuation of said visual, audible and/or tactile indicator device relative to the end of injection, said retarding system including a dashpot containing a fluid, a piston being arranged in said dashpot, one of said dashpot and of said piston being movable in translation in said body during actuation of said retarding system, and the other of said dashpot and of said piston being stationary relative to said body during actuation of said retarding system, the movement in translation of one relative to the other moving said fluid out from said dashpot through at least one flow passage, such that said movement in translation is braked, said retarding system comprising said dashpot containing said fluid, said piston, a locking key, said injection spring, a pusher element, a support member interposed between said pusher element and said injection spring, and said piston rod.

Advantageously, during actuation of said retarding system, said piston is movable in translation in said body, and said dashpot is stationary.

Advantageously, during actuation of said retarding system, said dashpot is prevented from moving in translation by a second frustoconical or sloping wall portion of said body that co-operates with at least one flexible tab of said dashpot, said piston, during actuation of said retarding system, preventing said flexible tabs from deforming radially inwards.

Advantageously, after actuating said retarding system, said piston is moved axially relative to said at least one flexible tab of said dashpot and no longer prevents it from deforming radially inwards, such that said dashpot is no longer prevented from moving in translation in said body.

Advantageously, said at least one flow passage is formed by an axial groove in the dashpot.

Advantageously, said at least one flow passage is formed by a central hole in the piston.

Advantageously, said pusher element is axially movable in said body and co-operates with said piston, such that an axial movement of said pusher element causes an axial movement of said piston in said dashpot.

Advantageously, said locking key comprises a head, a longitudinal rod, and an endpiece that is adapted to co-operate with the piston rod, said head of the locking key being in its blocking position before triggering the retarding system, in which position it co-operates with a recess of said pusher element.

Advantageously, when the piston rod arrives towards its end-of-injection position, it co-operates with the endpiece of the locking key so as to pull said locking key axially downwards out from its blocking position, such that said pusher element is thus no longer prevented from moving in translation by said locking key.

Advantageously, said pusher element includes flexible tabs that, before actuation of the retarding system, co-operate with a first frustoconical or sloping wall of the body, the head of the locking key, in its blocking position, preventing said flexible tabs from deforming radially inwards.

Advantageously, said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

Advantageously, said reservoir includes a needle through which said fluid is injected into said injection site.

These characteristics and advantages and others of the present invention appear more clearly from the following detailed description, given by way of non-limiting examples, and with reference to the accompanying drawings, and in which.

Figure 20A:
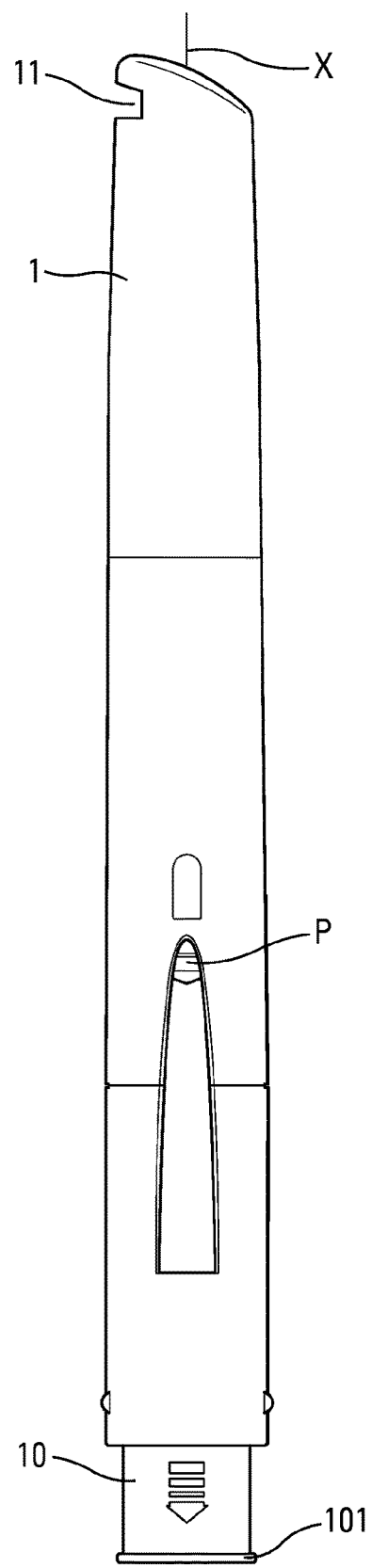
FIGS. 20a and 20b are diagrammatic views, respectively from the side and in section, of an autoinjector constituting another embodiment, in its rest position, before-pricking.
Figure 20B:
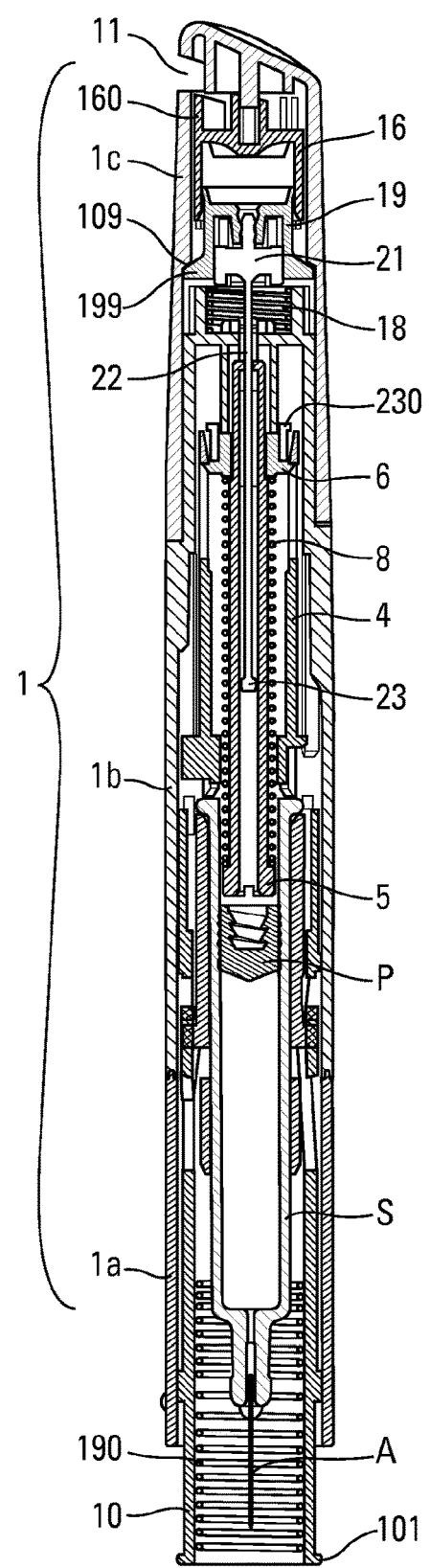
Figure 21A:
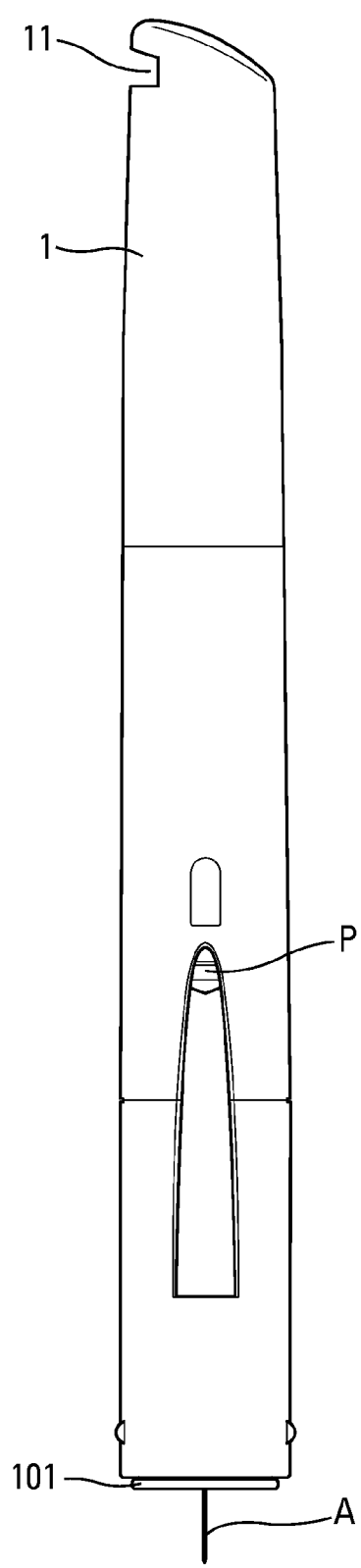
FIGS. 21a and 21b are views similar to the views in FIGS. 20a and 20b, in the after-pricking and before-injection position.
Figure 21B:
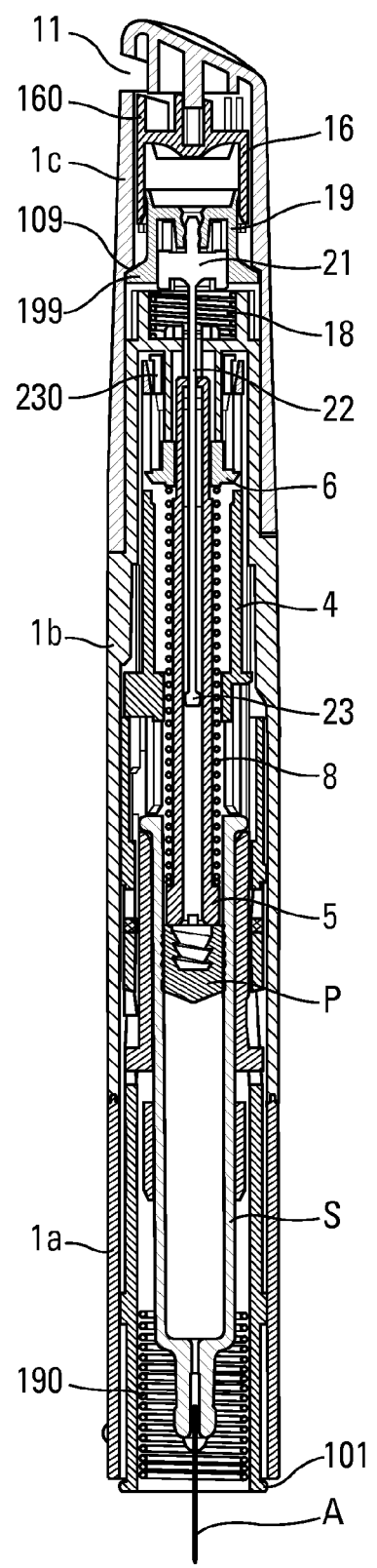
Figure 22A:
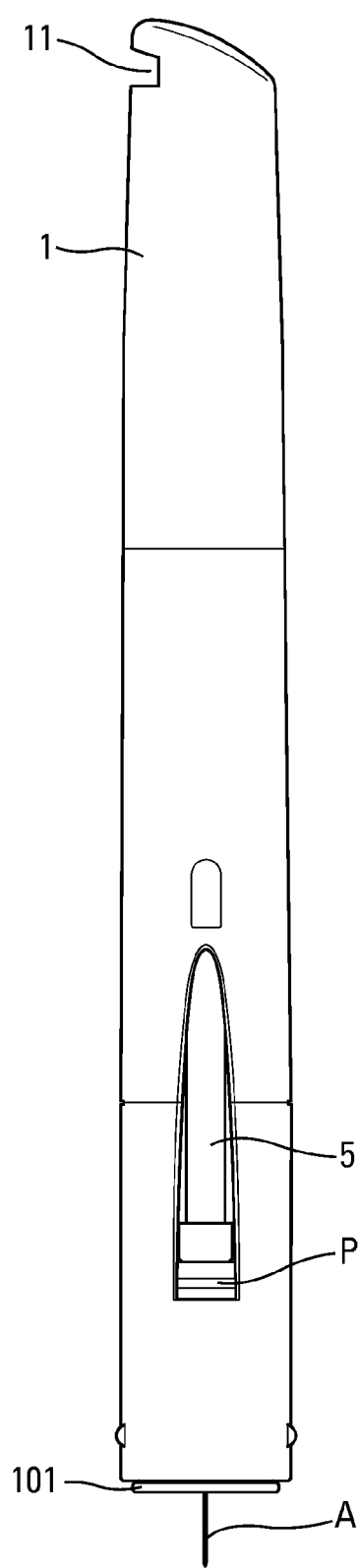
FIGS. 22a and 22b are views similar to the views in FIGS. 21a and 21b, in the just prior to the end of injection position and at the moment at which the retarding system is triggered.
Figure 22B:
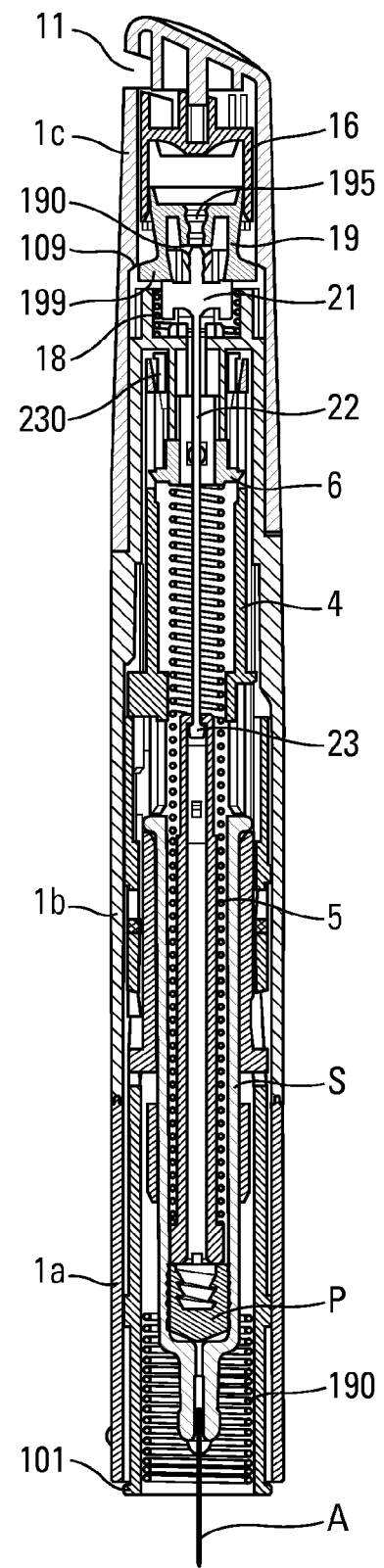
Figure 23A:
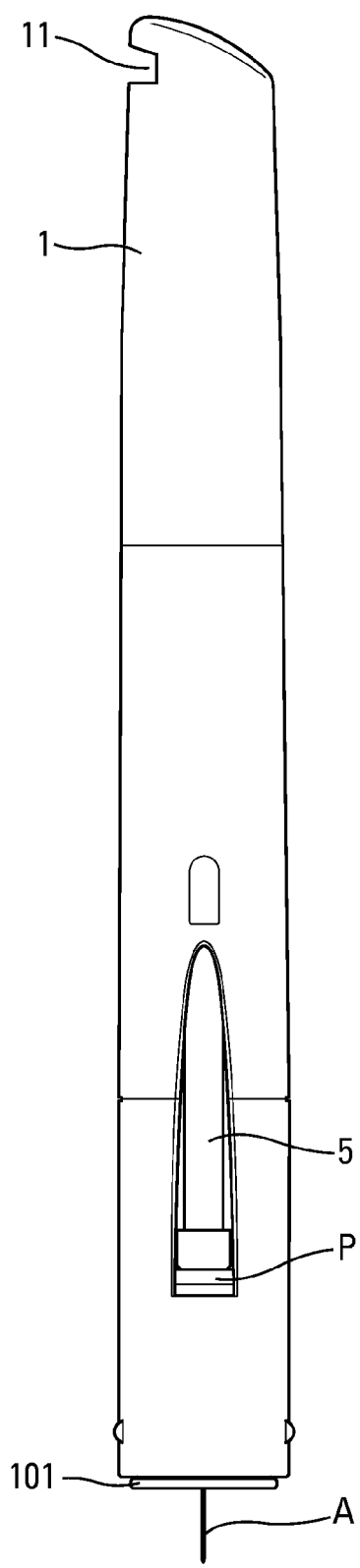
FIGS. 23a and 23b are views similar to the views in FIGS. 22a and 22b, at the beginning of actuating the retarding system.
Figure 23B:
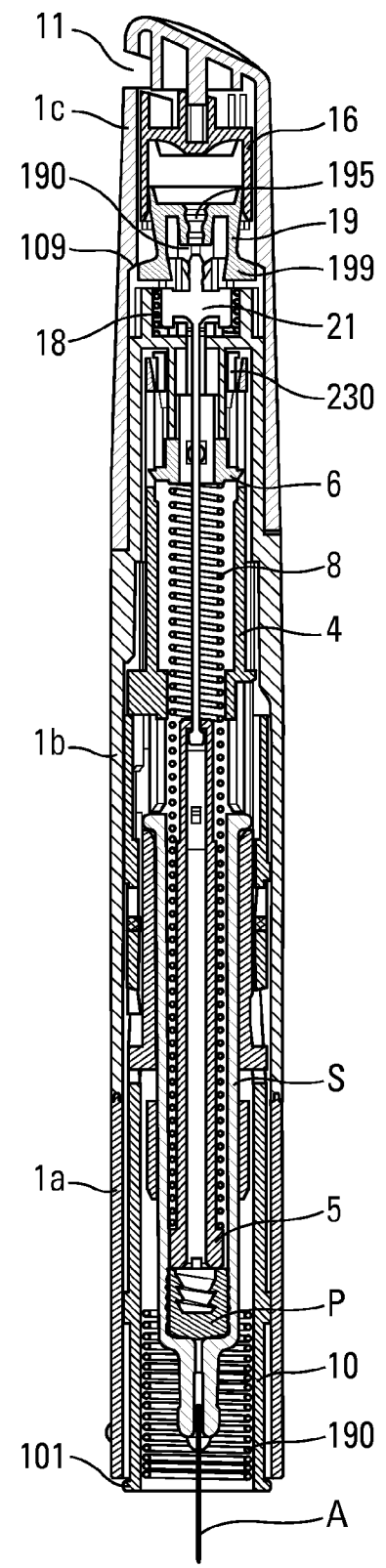
Figure 24A:
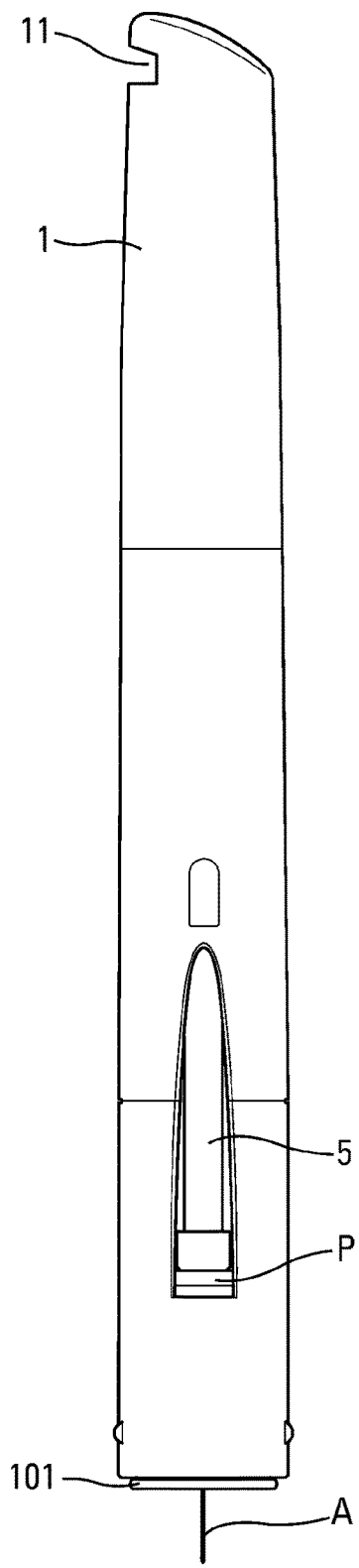
FIGS. 24a to 24b are views similar to the views in FIGS. 23a to 23b, at the end of actuating the retarding system.
Figure 24B:
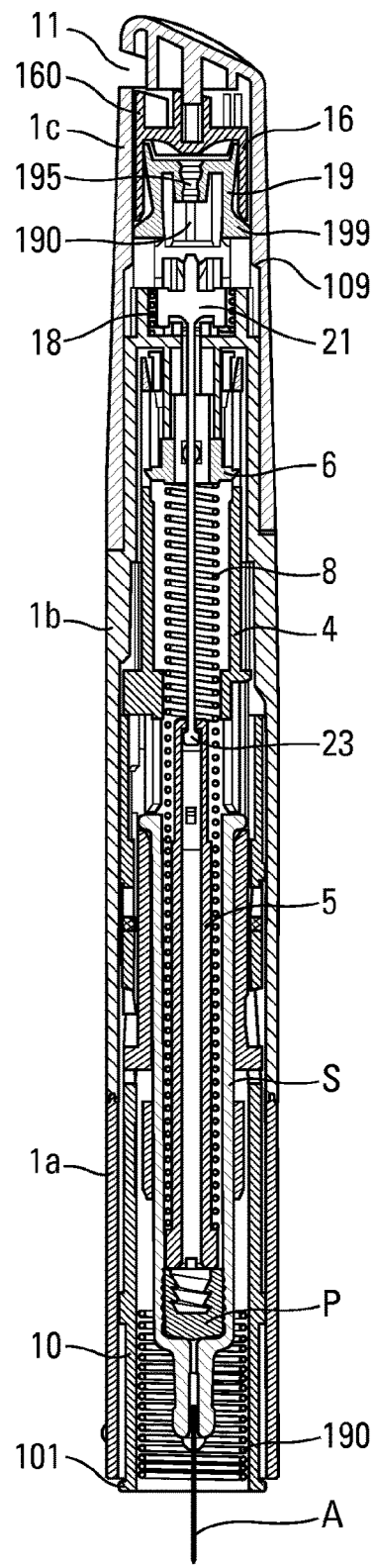
Figure 24C:
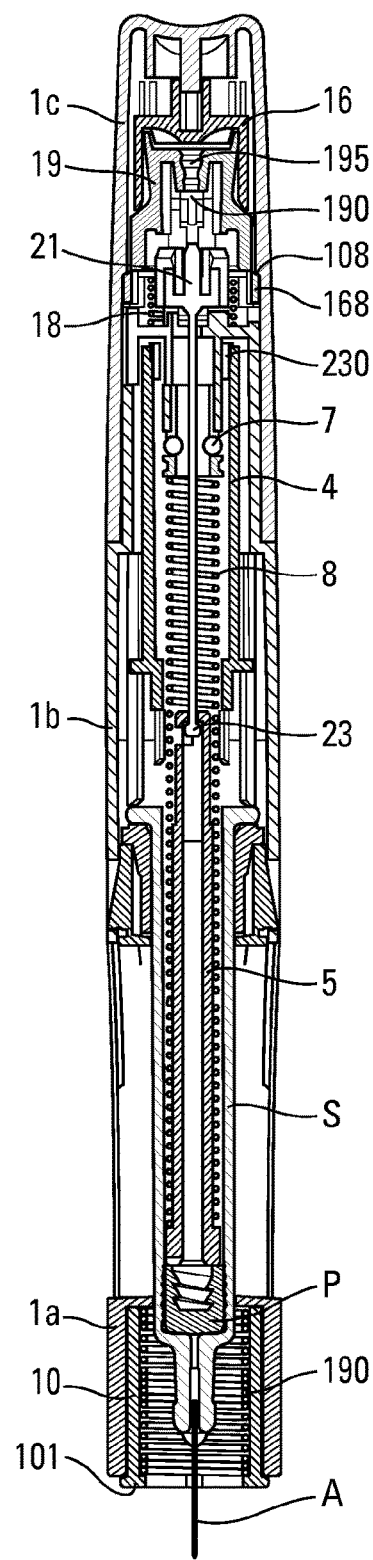
FIG. 24c is a view similar to the view in FIG. 24b on another section plane.
Figure 25A:
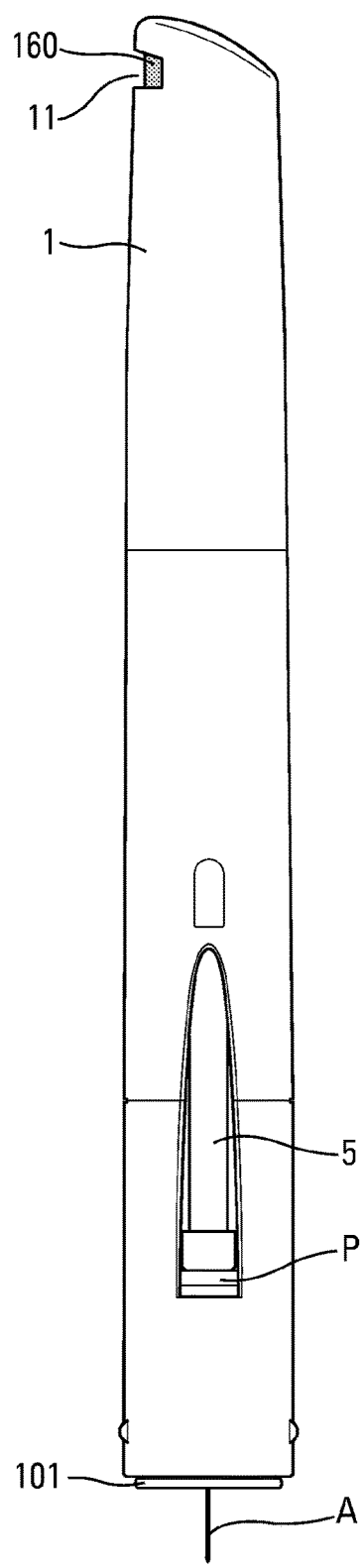
FIGS. 25a to 25c are views similar to the views in FIGS. 24a to 24c, at the end of actuating the indicator device, and before the autoinjector has been removed from the injection site.
Figure 25B:
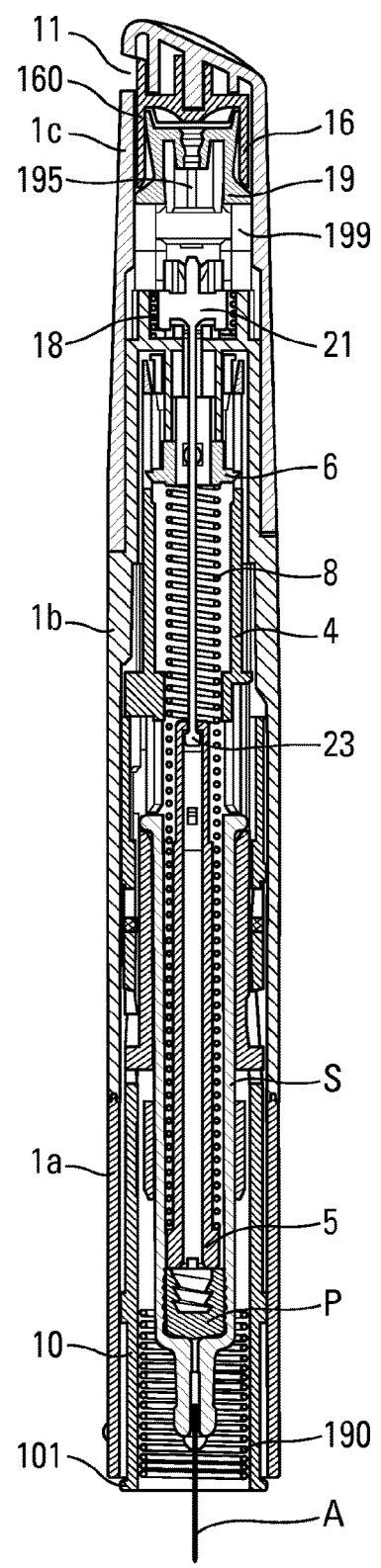
Figure 25C:
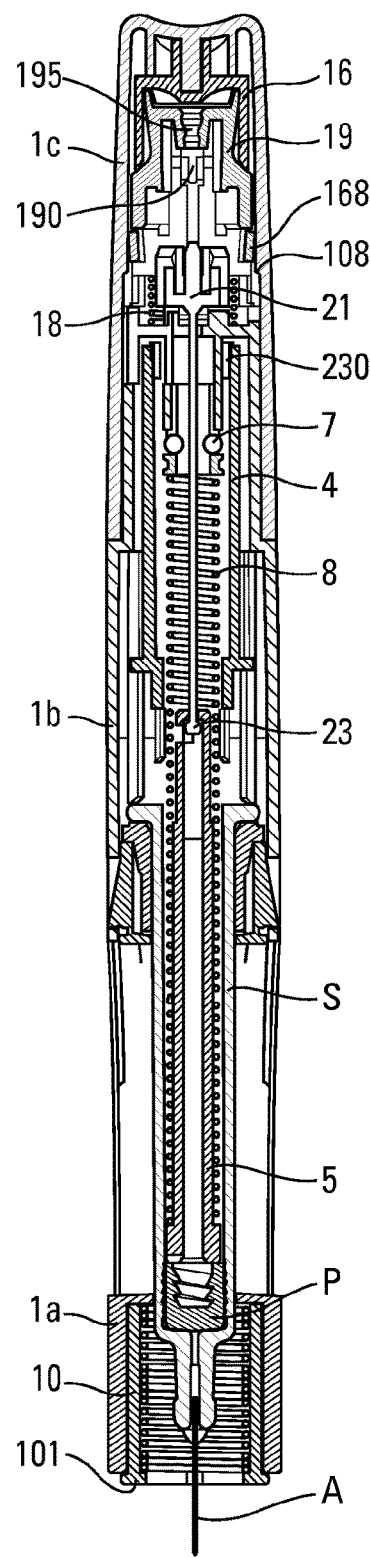

In the following description, the terms "top", "bottom", "high", and "low" refer to the positions shown in FIGS. 1a to 7, 17, 18, and 20a to 26. The terms "axial" and "radial" refer to the longitudinal central axis X, shown in particular in FIGS. 1a and 20a, that corresponds to the longitudinal axis of the needle.

The autoinjector is described below with reference to two advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

The autoinjector shown in the figures comprises a body 1 in which an actuator sleeve 10 slides axially, the actuator sleeve 10 having a bottom end 101 that is for coming into contact with the body of the patient around the injection zone. In the embodiment in FIGS. 1 to 19, the autoinjector includes a lower body 1a and an upper body 1c that are assembled together so as to form the body 1 of the autoinjector. In the embodiment in FIGS. 20 to 34, the autoinjector includes a lower body 1a, an intermediate body 1b, and an upper body 1c that are assembled together so as to form the body 1 of the autoinjector. Below, the term "body" and the numerical reference "1" are used to designate said unitary body formed by assembling said lower body 1a with said intermediate body 1b and/or said upper body 1c. It should be observed that the body 1 could be formed of any number of body portions, and that the embodiments in the figures, with two or three body portions, are not limiting.

A reservoir S may be inserted into said body 1 of the autoinjector, said reservoir S preferably being stationary in said body 1. The reservoir S contains fluid and includes a piston P and a needle A. The piston P is adapted to move in said reservoir S so as to inject the fluid through said needle A. Optionally, the present invention could also apply to a reservoir that does not have a needle, in particular in an injection device that does not have a needle.

The present description is made with reference to a syringe S that may be of any type. More generally, it is understood that the term "syringe" in the present description encompasses any type of reservoir associated with a needle. Preferably, the reservoir S is a pre-filled syringe.

Before the autoinjector is actuated, the needle A of the syringe S can be protected by a guard (not shown), the autoinjector possibly including a cap (not shown) that the user can remove before actuation. Removal of the cap advantageously causes the guard to be removed.

Figure 1A:
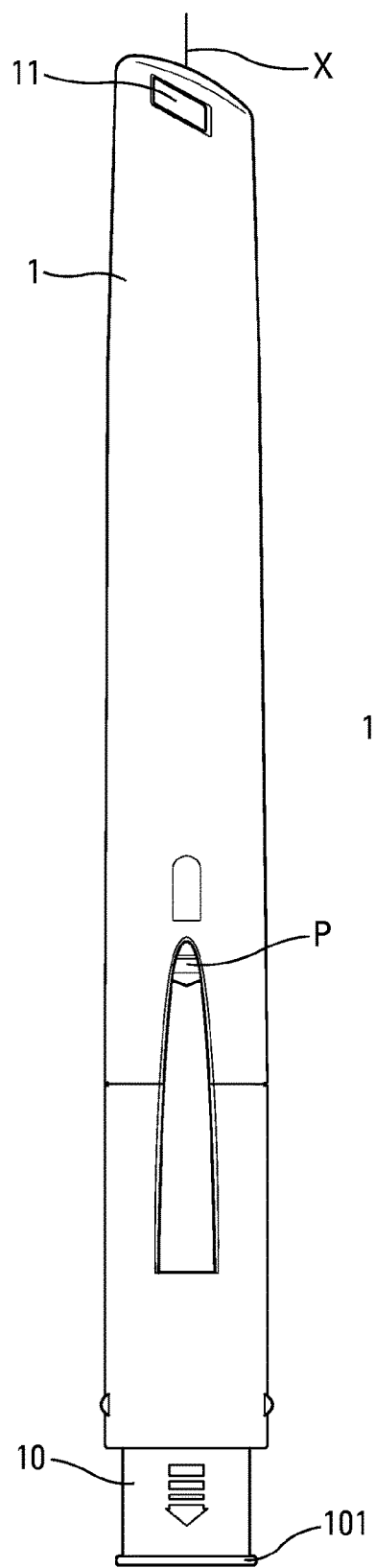
FIG. 1a is a diagrammatic side view of an autoinjector constituting an advantageous embodiment of the present invention, in its rest position, before-pricking.
Figure 1B:
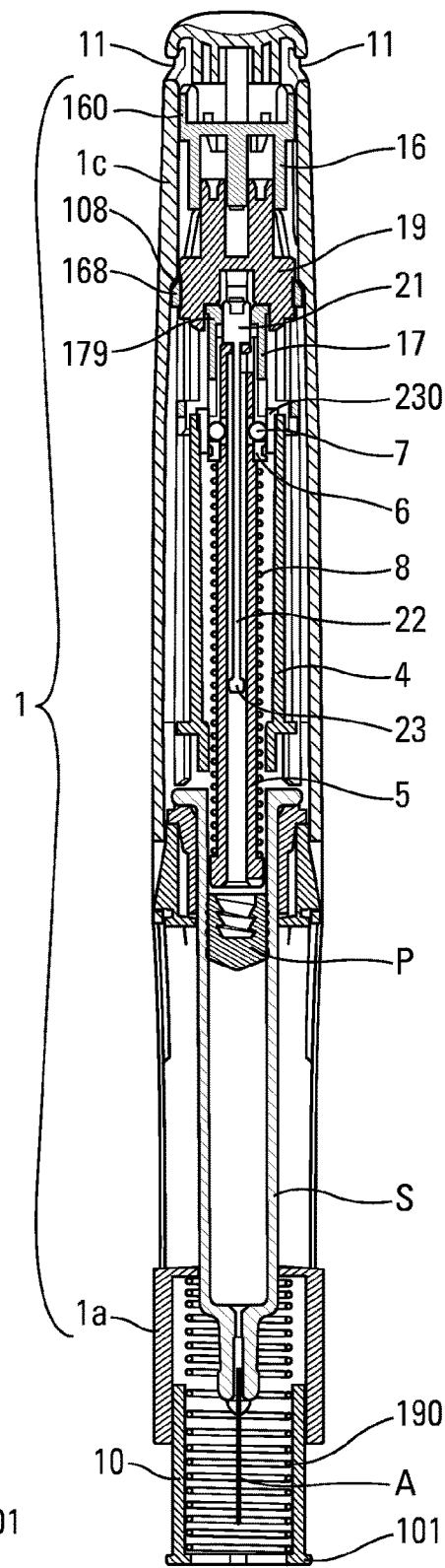
FIGS. 1b and 1c are views similar to the view in FIG. 1a, in section, on two different section planes.
Figure 1C:
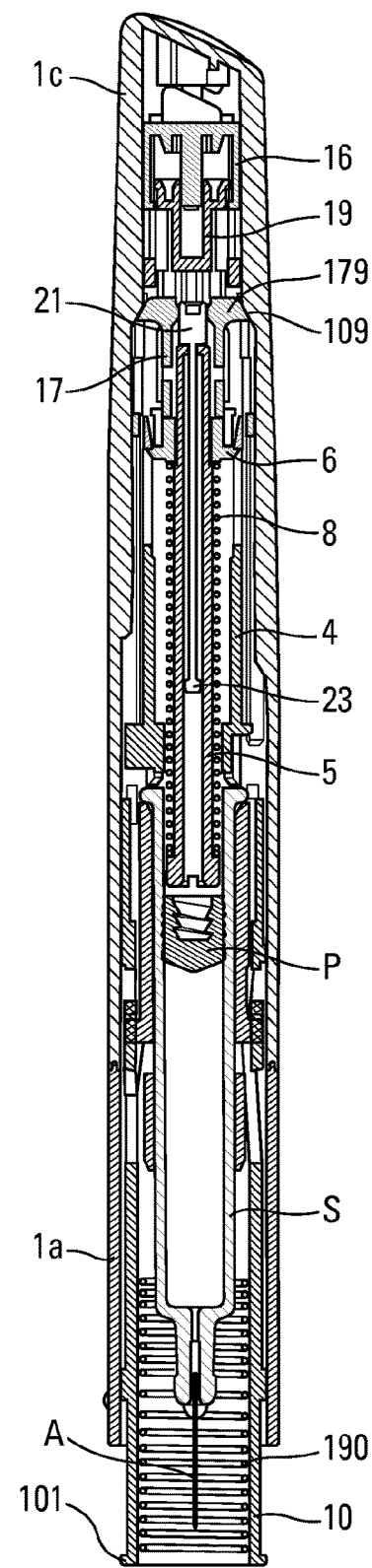
Figure 2A:
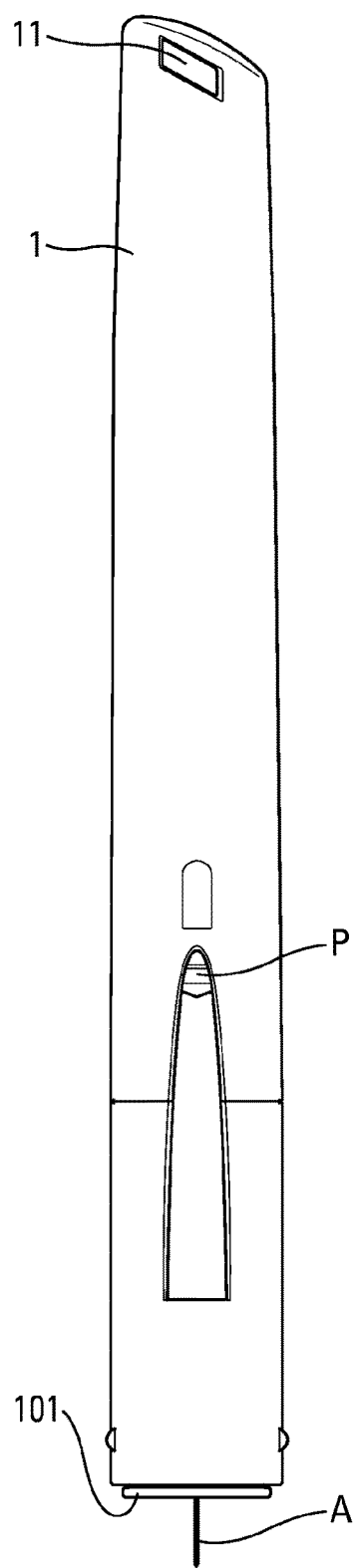
FIGS. 2a to 2c are views similar to the views in FIGS. 1a to 1c, in the after-pricking and before-injection position.
Figure 2B:
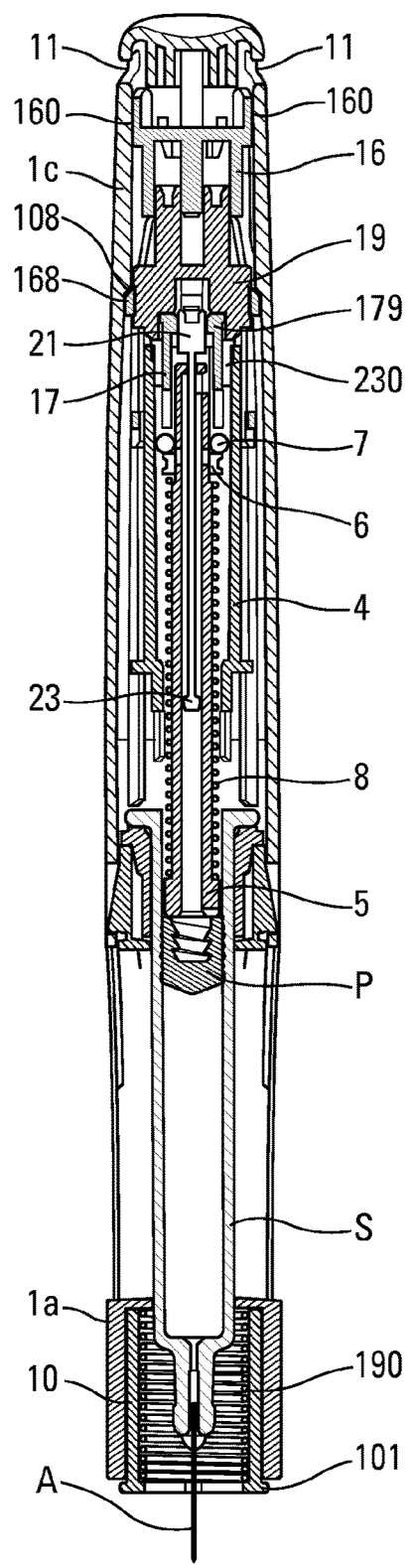
Figure 2C:
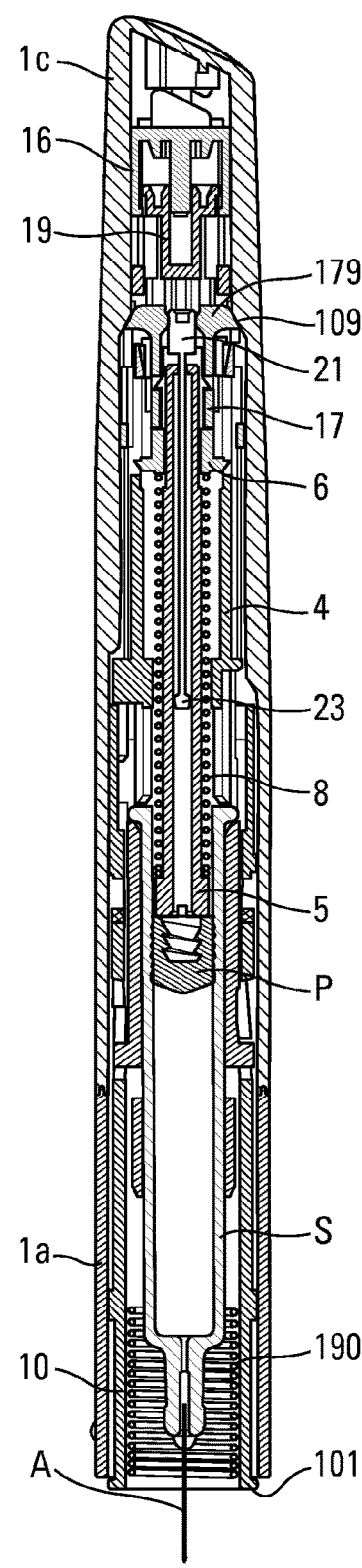
Figure 3A:
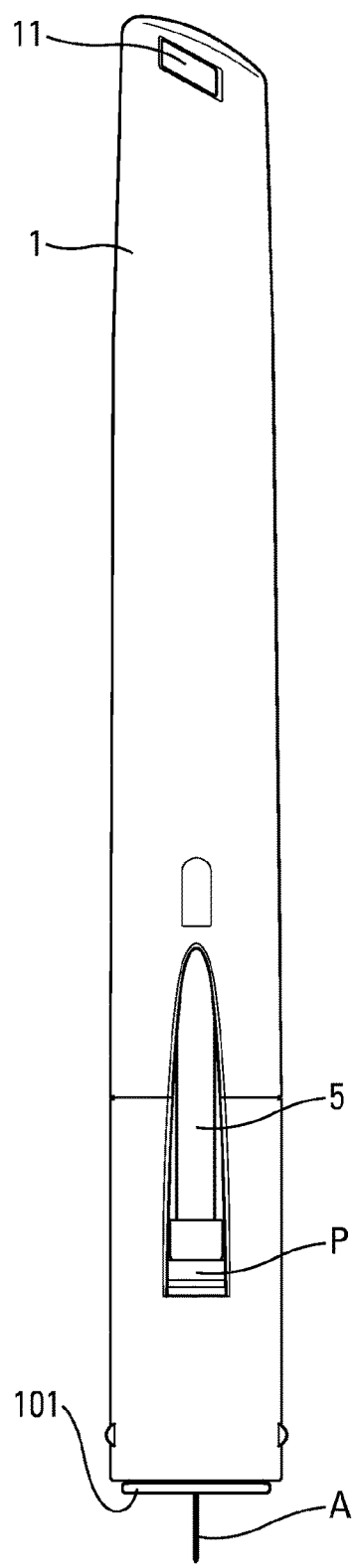
FIGS. 3a to 3c are views similar to the views in FIGS. 2a to 2c, in the just prior to the end of injection position and at the moment at which the retarding system is triggered.
Figure 3B:
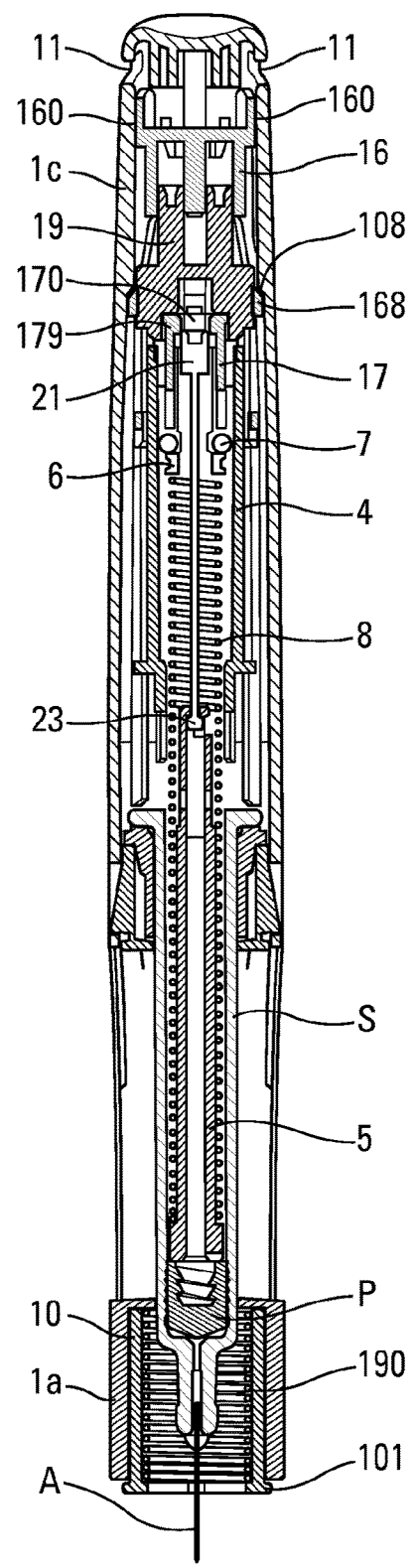
Figure 3C:
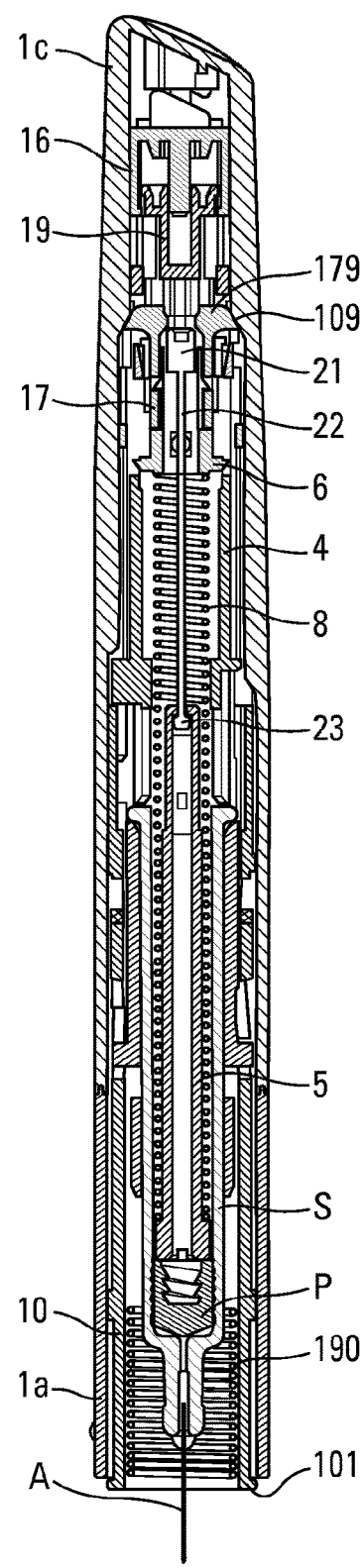
Figure 4A:
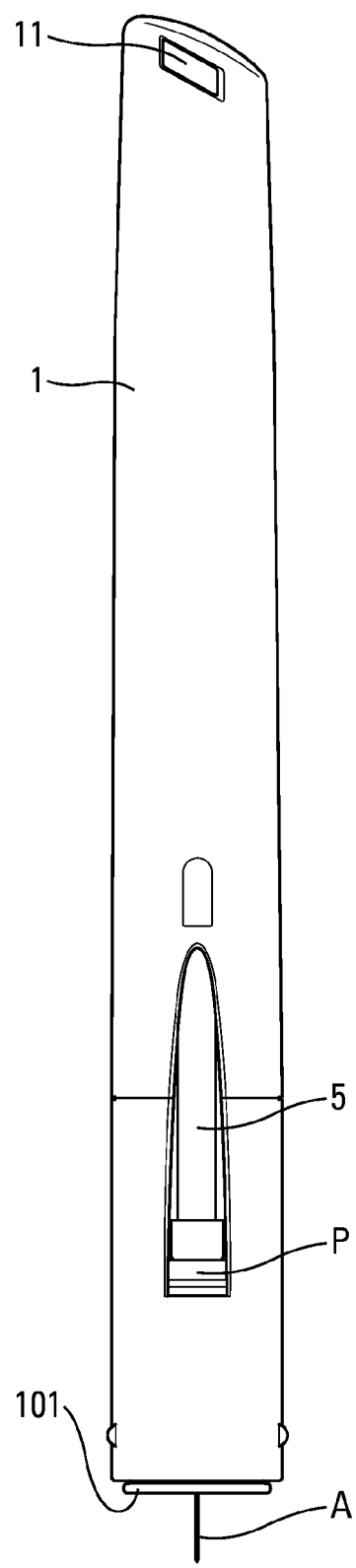
FIGS. 4a and 4b are views similar to the views in FIGS. 3a and 3c, at the beginning of actuating the retarding system.
Figure 4B:
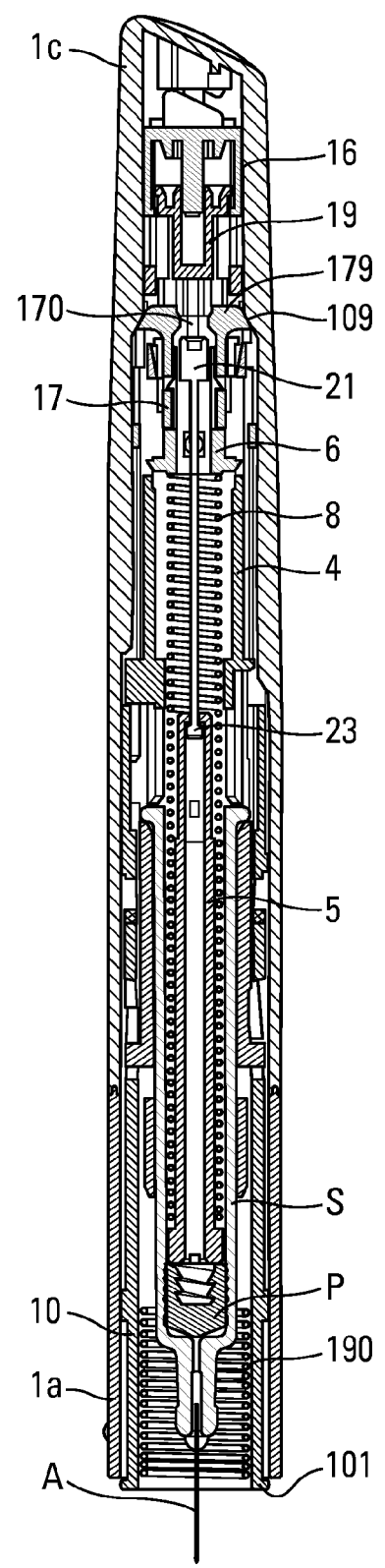
Figure 5A:
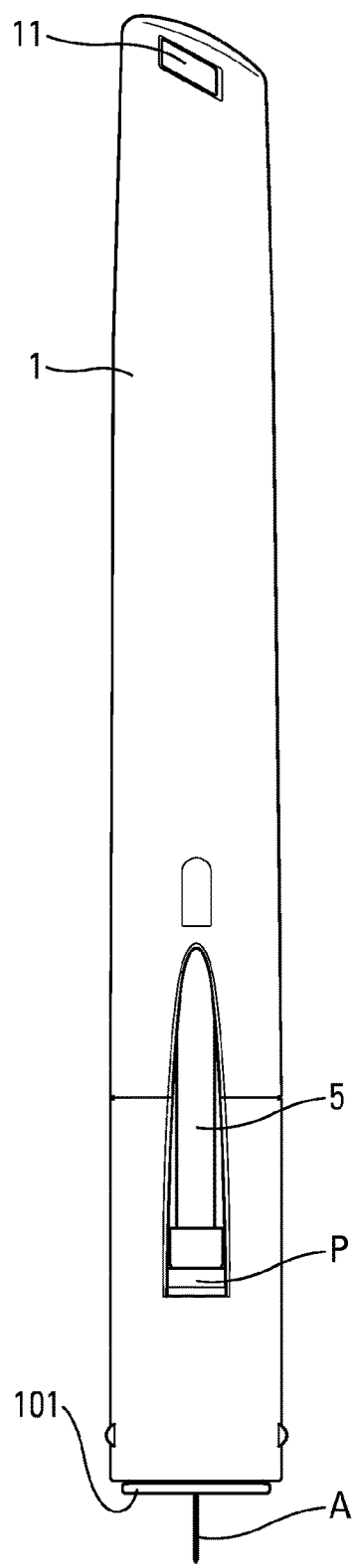
FIGS. 5a to 5c are views similar to the views in FIGS. 3a to 3c, at the end of actuating the retarding system.
Figure 5B:
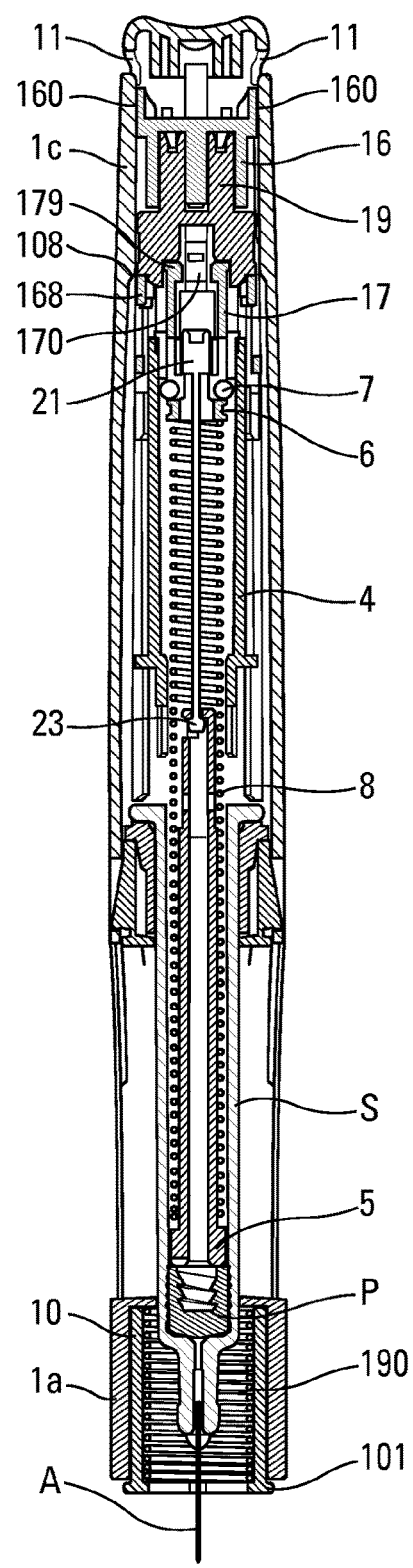
Figure 5C:
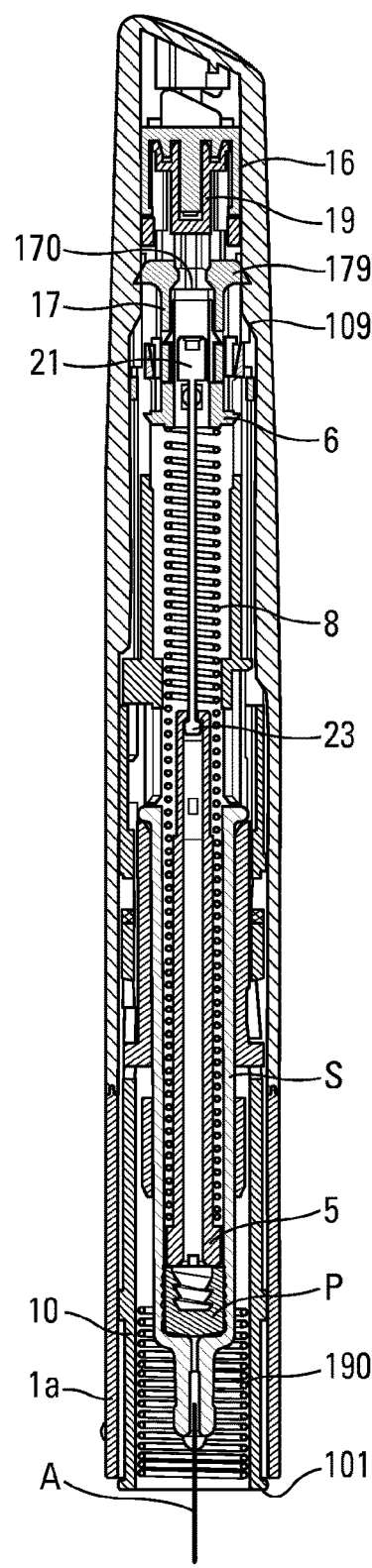

Before actuation, the actuator sleeve 10 is in a first projecting position in which it surrounds the needle A, as shown in FIGS. 1*a* and 1*b* firstly, and 20*a* and 20*b* secondly. During actuation, the actuator sleeve 10 slides inside the body 1 towards an actuated position, so as to expose the needle A and enable pricking, and then injection of the fluid.

Figure 6A:
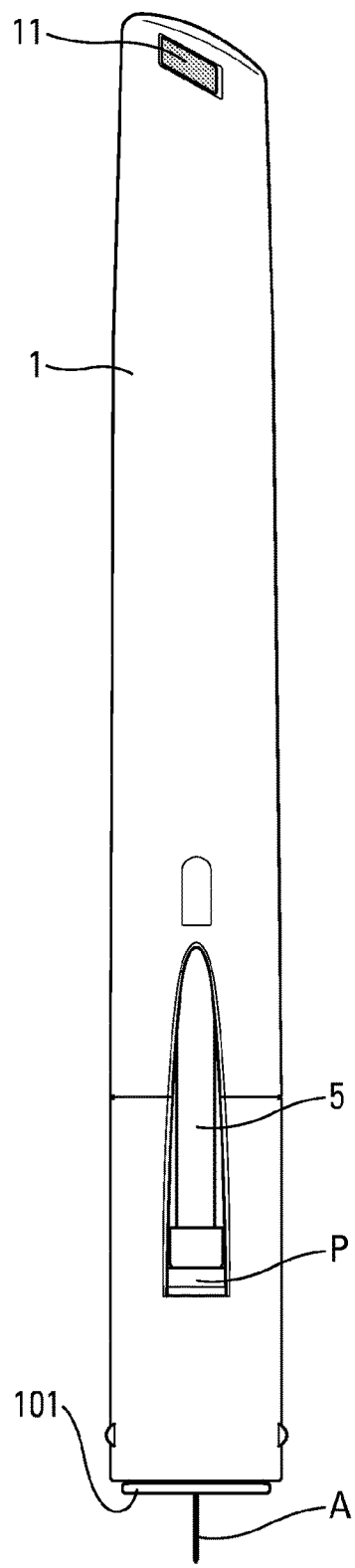
FIGS. 6a to 6c are views similar to the views in FIGS. 3a to 3c, at the end of actuating the indicator device, and before the autoinjector has been removed from the injection site.
Figure 6B:
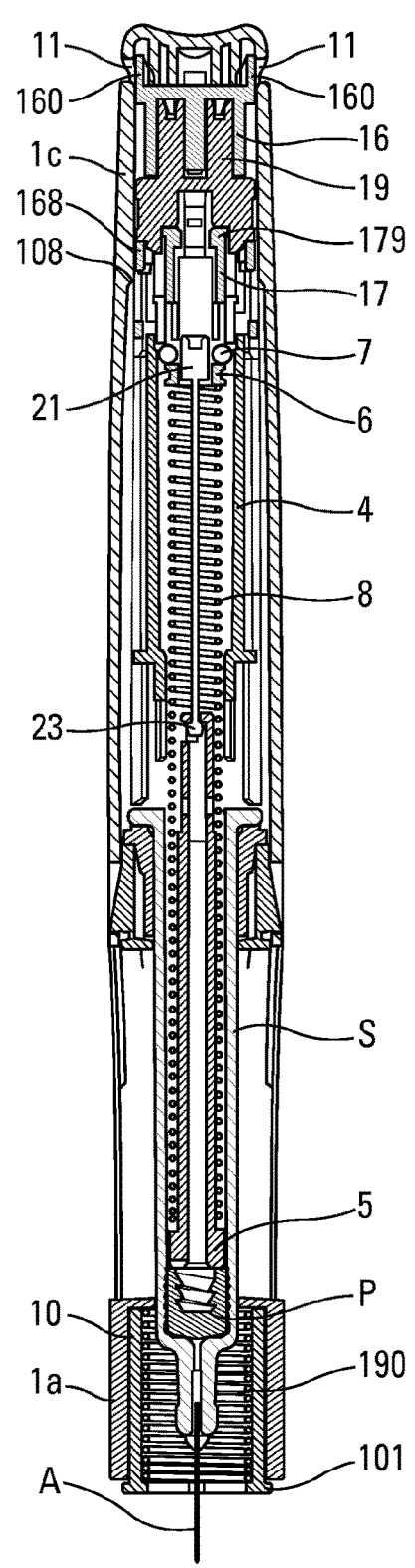
Figure 6C:
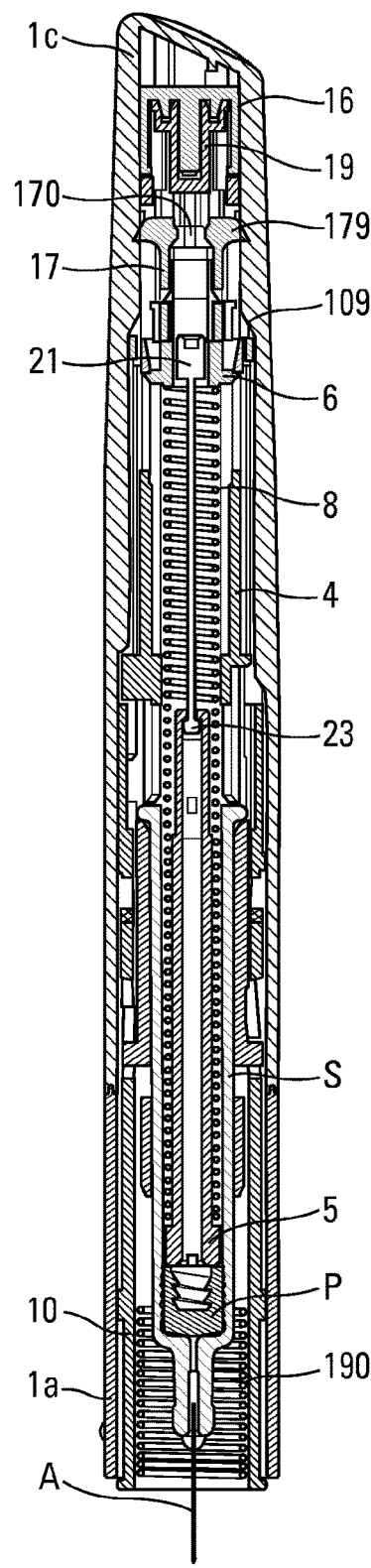
Figure 7:
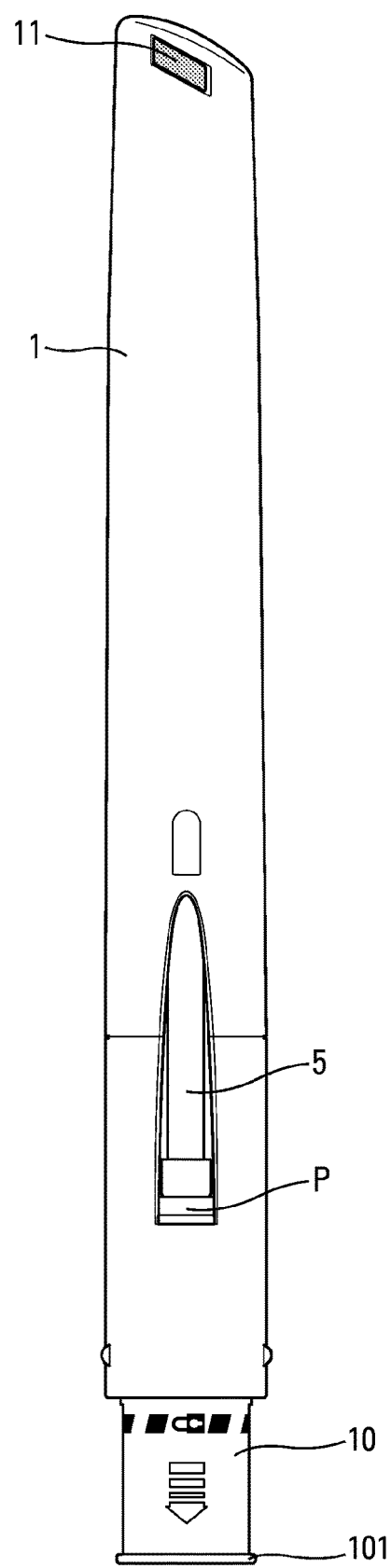
FIG. 7 is a view similar to the view in FIG. 6a, in the end-of-use position, after the autoinjector has been removed from the injection site.
Figure 26:
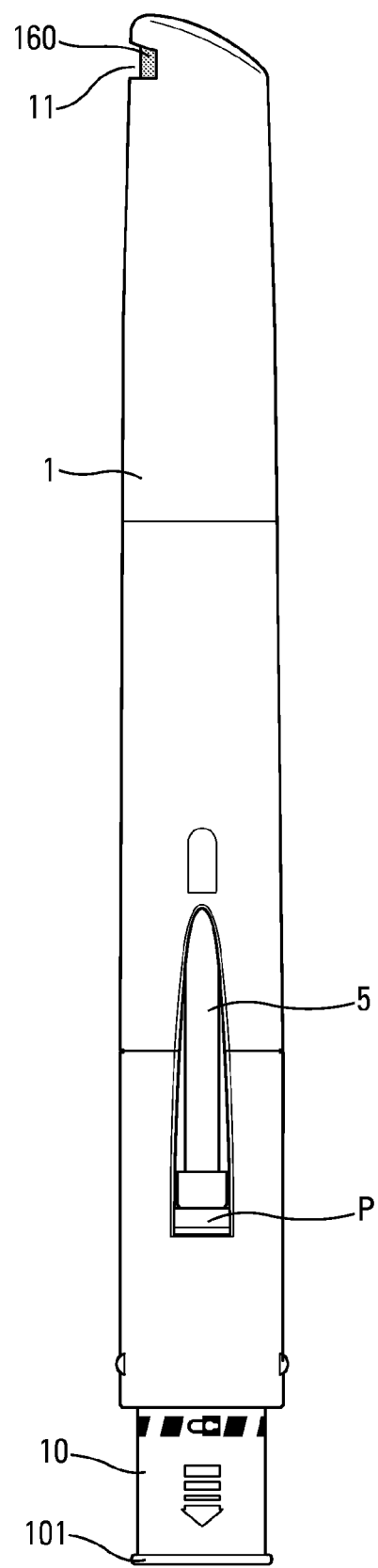
FIG. 26 is a view similar to the view in FIG. 25a, in the end-of-use position, after the autoinjector has been removed from the injection site.

After injection, when the user removes the autoinjector from the injection site, the actuator sleeve 10 returns into an end-of-use second projecting position in which it is once again arranged around the needle A, so as to avoid any risk of injury with said needle, as shown in FIGS. 6 and 26.

The actuator sleeve 10 is advantageously urged towards its projecting positions by a resilient member or spring 190 that may be of any type. Advantageously, in said end-of-use position, said actuator sleeve 10 is locked, and can no longer be moved axially into said body 1. By way of example, locking may be achieved by tabs (not shown) that are secured to the body 1 or to the reservoir S, and that co-operate with openings (not shown) in said actuator sleeve 10 when said actuator sleeve reaches its second projecting position. Locking, that is not essential to the operation of the present invention, is not described in greater detail below. It could be achieved in ways that are different from the particular embodiment mentioned above. In particular, it could be achieved in accordance with the teaching of documents WO 2013/175140 or WO 2013/175142.

The autoinjector also includes an automatic injection system, in particular comprising a piston rod 5 that is adapted to co-operate with the piston P so as to move it in the reservoir S so as to dispense the fluid through the needle A. Conventionally, the piston rod 5 is urged by an injection spring 8 towards its dispensing position and, before actuation, it is held in its rest position by an appropriate injection lock.

An advantageous injection lock is described in particular in document WO 2015/155484.

The lock may comprises at least one blocking element 7 that is held in its blocking position by a blocking ring 230 that is fastened, in particular snap-fastened, on a support member 6 against which the injection spring 8 bears. Triggering said injection lock causes said injection means to be actuated, and thus fluid to be injected through the needle. Said injection lock may further include a control sleeve 4 that is arranged in said body 1, said control sleeve 4 containing said piston rod 5 and said injection spring 8, said piston rod 5 including a radial recess that receives at least one blocking element 7 that is movable between a blocking position and an unblocking position. Said at least one blocking element 7 is preferably of shape that is substantially spherical, such as a ball. Advantageously, said balls are urged radially outwards by said piston rod 5 and they are held in their blocking position by the blocking ring 230. The blocking ring 230 is axially movable relative to said piston rod 5 and relative to said support member 6 between a locking position in which it holds said balls in their blocking position, and an unlocking position in which said balls are released thereby unblocking said injection lock, enabling said injection spring 8 to move said piston rod 5 towards its injection position. In particular, the blocking ring 230 may be moved towards its unlocking position by said control sleeve 4.

When the needle A of the syringe S has penetrated the user's body, the blocking ring 230 is moved axially upwards, thereby causing the balls 7 to be released from their blocking position, said balls then moving radially outwards. The piston rod 5 is then no longer held by the balls, and it is thus moved axially downwards so as to inject the fluid.

The autoinjector includes a visual, audible, and/or tactile indicator device for indicating to the user, in particular by an audible sound, by vibration, and/or by visual and/or tactile indication, that the autoinjector may be removed from the injection site. Said visual, audible, and/or tactile indicator device is preferably arranged at the rear end of said body 1, remote from said injection site. In particular, in the embodiments shown, the indicator device includes an indicator element that gives visual indication, by a suitable display 160 in one or more windows 11 of the body 1. Advantageously, audible and/or tactile indication can also be provided, as described in greater detail below.

In order to avoid the user removing the autoinjector from the injection site as soon as injection ends, the autoinjector includes a retarding system that delays actuating said indicator device relative to the end of injection.

FIGS. 8 to 19 show a retarding system of an advantageous embodiment of the invention, and FIGS. 27 to 34 show a retarding system of another advantageous embodiment.

The main purpose of the retarding system is to put off starting the visual, audible, and/or tactile indication after the end of injecting the fluid into said body. In particular, this enables the fluid to diffuse for a few seconds after it has been injected. Such a retarding system also provides a benefit for the user, who no longer has to count, e.g. up to 10, after being injected, where it is possible that the time taken to perform such counting might vary greatly from one user to another. With a retarding system, the sequence of using an autoinjector is facilitated.

The mechanical retarding system thus makes it possible to put off starting the end-of-use indicator by a few seconds relative to the end of injection, this delay being predeterminable.

The invention makes use of the phenomenon of fluid transfer for generating said delay, and uses a dashpot 16, a piston 19 that slides axially in said dashpot 16, and a fluid arranged in said dashpot 16 and adapted to be moved by said piston 19, when said piston moves in said dashpot 16.

In the embodiments shown, during actuation of the retarding system, the dashpot 16 is stationary relative to the body 1, and the piston 19 is axially movable relative to said dashpot 16. However, the inverse configuration can also be envisaged.

A fluid is arranged in said dashpot 16, axially above said piston 19, said fluid being adapted to flow out from said dashpot while said piston 19 is being moved in said dashpot 16. The fluid may flow into another chamber of the dashpot or merely out from said dashpot. It may flow through one or more flow passages that are dimensioned so as to brake the movement of said piston 19 in said dashpot 16.

Depending on the viscosity of the fluid contained in the dashpot 16 and/or depending on the shapes and dimensions of the dashpot 16, of the piston 19, and/or of the flow passages, it is possible to adjust said braking quite accurately, and thus to adjust the time between the beginning and the end of actuating the retarding system. At the end of actuating the retarding system, the dashpot 16 may move axially in the body 1 so as to provide the indication, and in particular to indicate in the window 11 of the indicator that the autoinjector may be removed from the injection site. Actuating the visual, audible, and/or tactile indicator device is thus delayed relative to the end of injection, thereby enabling the injected fluid to diffuse in the injection site during this period of delay.

Figure 8:
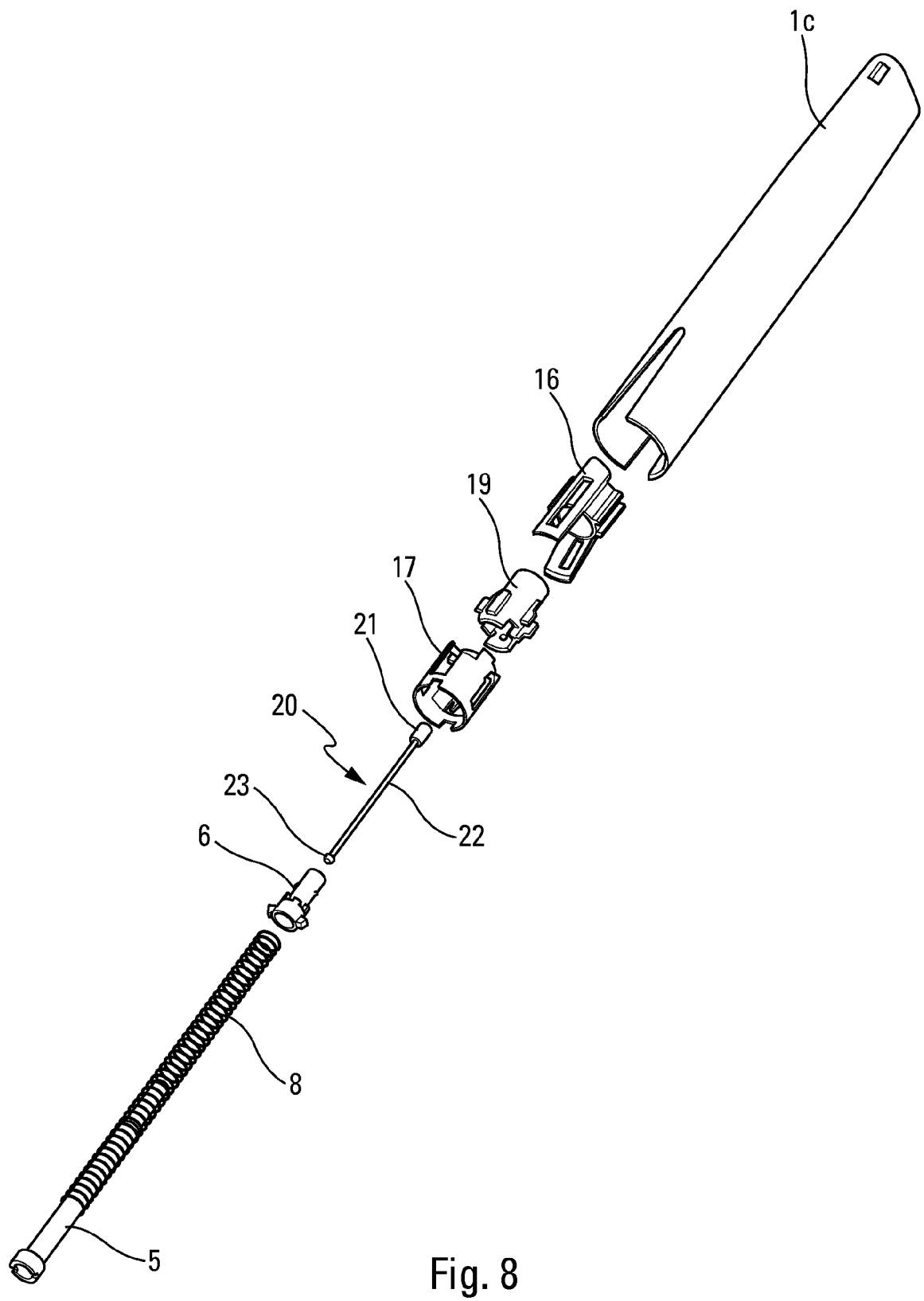
FIG. 8 is an exploded perspective view of the retarding system of said embodiment in FIGS. 1 to 7.
Figure 9:
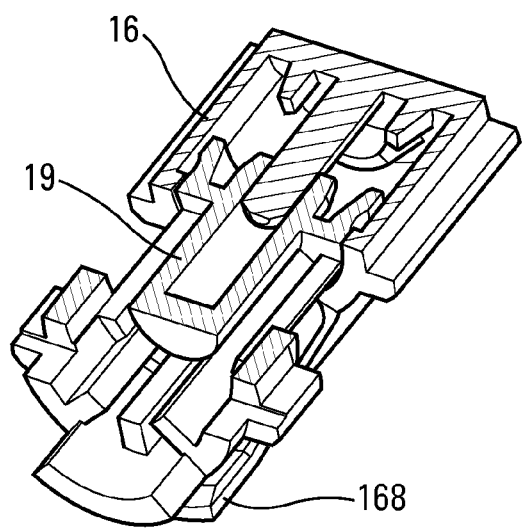
FIGS. 9 and 10 are fragmentary perspective views in section of the FIG. 8 system, showing the unit formed by the fluid dashpot and the piston, respectively before and during actuation of the retarding system.

FIG. 8 is an exploded diagrammatic perspective view of the retarding system of an advantageous embodiment of the invention. The retarding system comprises the upper body 1c, the dashpot 16 containing an appropriate fluid, the piston 19 that slides in said dashpot 16, a pusher element 17, a locking key 20, the piston rod 5, the support member 6, and the injection spring 8. The pusher element 17 is advantageously fastened, in particular snap-fastened, on said support member 6 of the injection lock.

In this embodiment, the body 1 is made up of only two portions, a lower body portion 1a and an upper body portion 1c. In this embodiment, there is thus no intermediate body portion.

In the embodiment shown, the dashpot 16 also forms an indicator element of the visual, audible, and/or tactile indicator device. Advantageously, said dashpot 16 may include an appropriate projection 160 for indicating the end of use of the autoinjector in one or more windows 11 of the body 1, in particular of the upper body 1c. In the embodiment shown in FIGS. 1 to 19, the body 1 includes a single window 11.

The pusher element 17 is axially movable in said body 1, and co-operates with said piston 19. While said piston 19 is being moved axially, the dashpot 16 is prevented from performing any axial movement. Thus, axial movement of said pusher element 17 causes axial movement of the piston 19 in the dashpot 16. In a variant, the inverse configuration could be envisaged, namely that the pusher element 17 moves a movable dashpot relative to a stationary piston.

The locking key 20 comprises a head 21 that is adapted to co-operate with the retarding system, a longitudinal rod 22, and an endpiece 23 that is adapted to co-operate with the piston rod 5.

In the position prior to triggering the retarding system, the head 21 of the locking key 20 is in its blocking position in which it co-operates with an axial recess 170 of the pusher element 17, such that said pusher element is prevented from moving in translation by said key. When the piston rod 5 comes towards its end-of-injection position, it co-operates with the endpiece 23 of the locking key 20, and thus pulls said locking key axially downwards. As a result, the head 21 of said locking key 20 moves axially out from said recess 170, such that said pusher element 17 is no longer prevented from moving in translation by said key 20.

The injection spring 8 urges the pusher element 17 to move axially in translation towards the rear of said upper body 1c. While the pusher element 17 is blocked by said locking key 20, the retarding system is thus also blocked.

Figure 16:
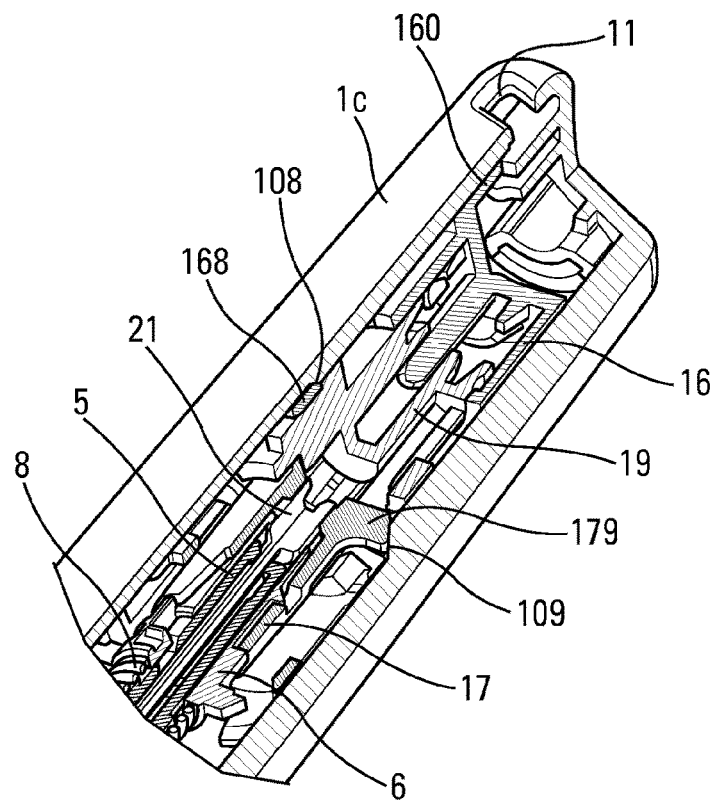
FIGS. 16 to 18 are cut-away perspective views of a detail of the FIG. 8 system, respectively before actuating, after actuating, and at the end of actuating the retarding system.

In the embodiment shown, before actuation of the retarding system, the pusher element 17 is prevented from performing any axially upward movement by a first frustoconical or sloping wall 109 of the upper body 1c, which wall co-operates with flexible tabs 179 of said pusher element 17. In the embodiment shown, there are two diametrically-opposite flexible tabs 179, but a different number of first flexible tabs could be envisaged, e.g. a single tab, or more than two tabs. As can be seen in FIG. 16 in particular, in its blocking position, said head 21 of the locking key 20 prevents said flexible tabs 179 of the pusher element 17 from deforming radially inwards. When said head 21 is no longer in its blocking position, said flexible tabs 179 can deform radially inwards under the effect of the injection spring 8 that pushes said pusher element 17 axially upwards, and as a result of the co-operation between said flexible tabs 179 and the first sloping wall 109 of the body 1.

Figure 10:
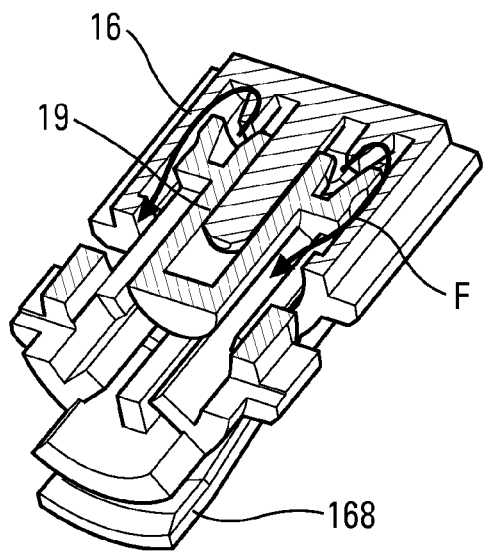
Figure 11:
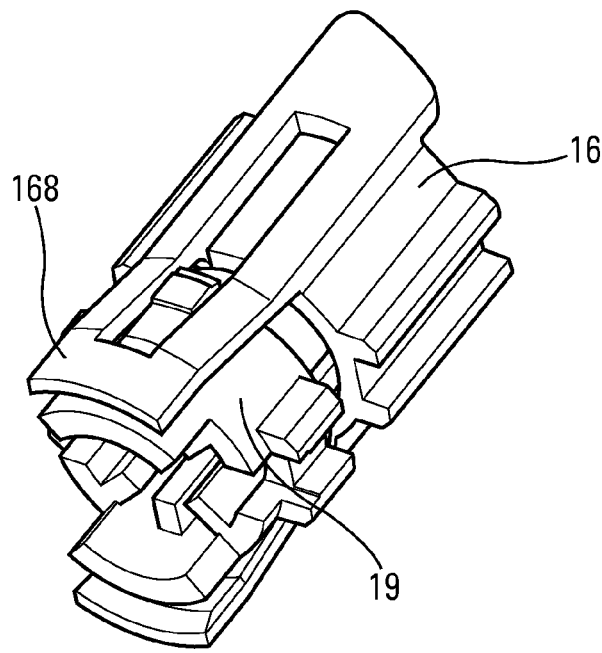
FIGS. 11 and 12 are perspective views of a detail of the unit formed by the fluid dashpot and the piston, after actuating the retarding system, respectively before and after the deformable tabs of the dashpot have been deformed.
Figure 12:
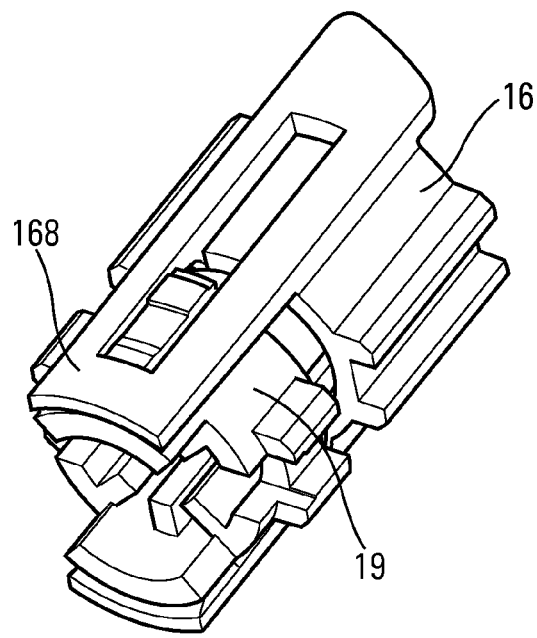
Figure 15:
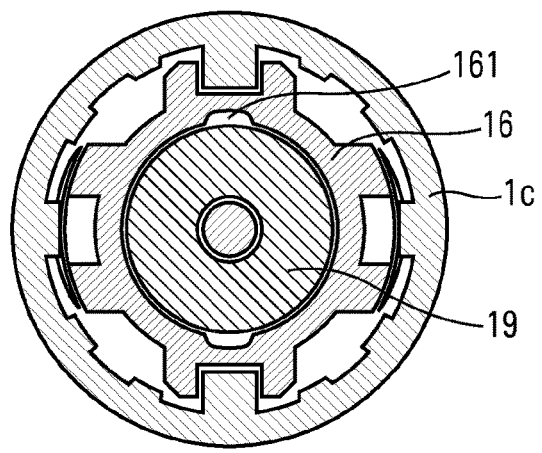
FIG. 15 is a diagrammatic horizontal section view on section plane A-A of FIG. 14.

When said locking key 20 releases said pusher element 17 at the end of injection, said pusher element is thus moved axially by said injection spring 8. The retarding system is thus triggered, with said pusher element 17 co-operating with said piston 19 so as to move it axially in said dashpot 16. This causes the fluid to be transferred out from said dashpot 16 through appropriate flow passages 161. In the embodiment shown, the flow passages are formed by axial grooves formed in said dashpot 16, as can be seen in FIG. 15 in particular. Arrows F in FIG. 10 show the transfer of fluid. The speed of axial movement of the pusher element 17 thus corresponds to the speed of axial movement of said piston 19 that is subjected to braking as a result of transferring the fluid out from the dashpot 16 through said flow passages 161.

Figure 13:
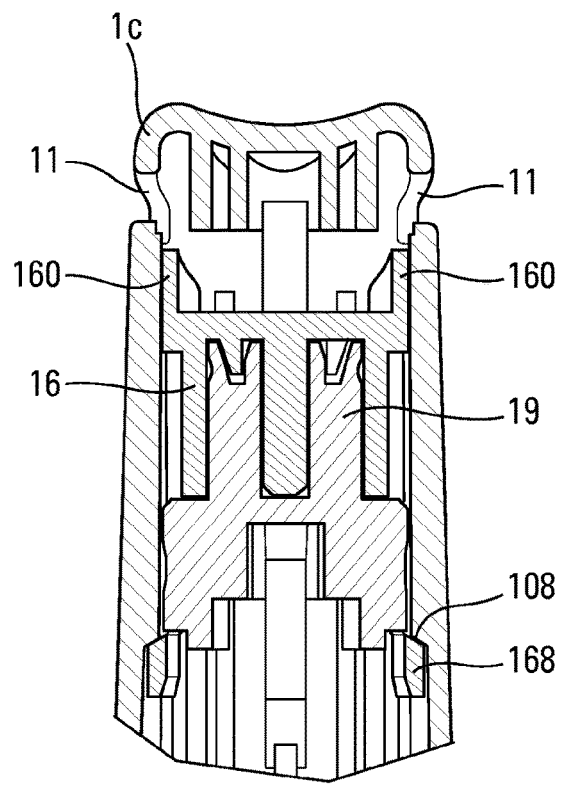
FIGS. 13 and 14 are views of a detail similar to the views in FIGS. 11 and 12, but in section, respectively before and after the deformable tabs of the dashpot have been deformed.
Figure 14:
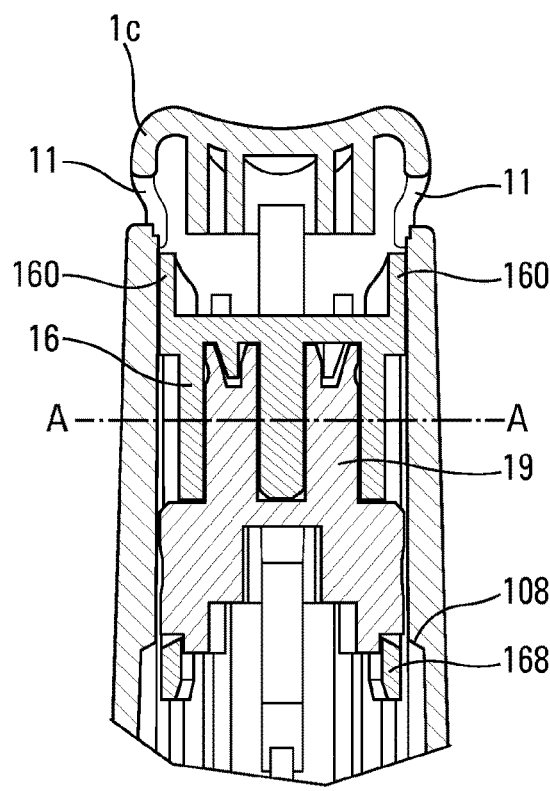
Figure 17:
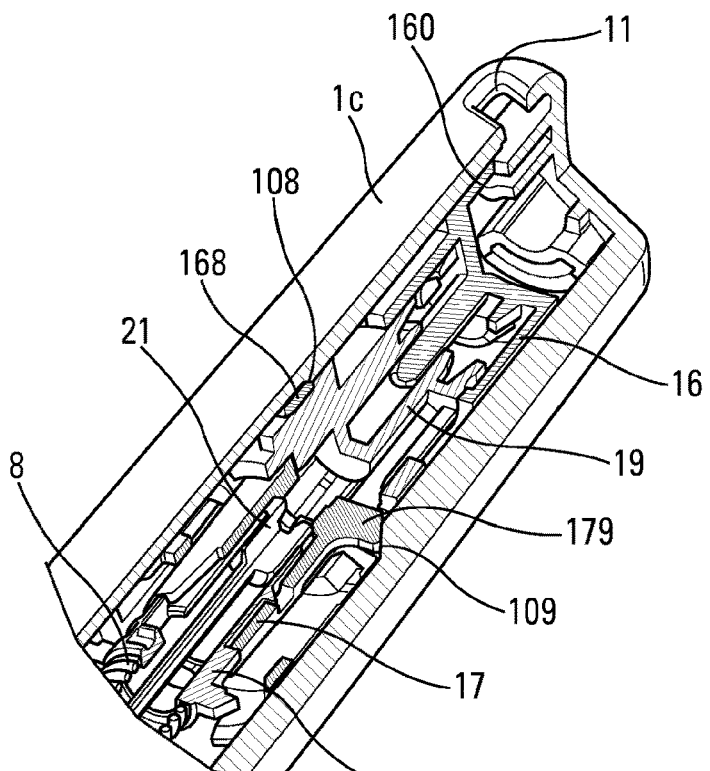
Figure 18:
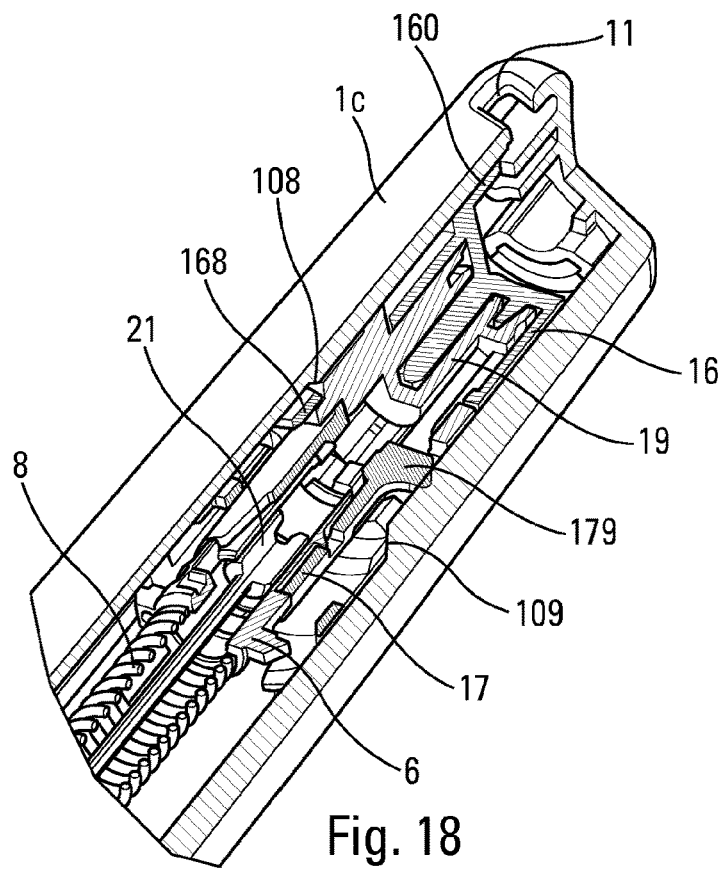

While said piston 19 is moving in said dashpot 16, said dashpot is prevented from performing any axial movement by flexible tabs 168 of said dashpot 16 that co-operate with a second sloping wall 108 of the body 1, as can be seen in FIG. 13. In the embodiment shown, there are two diametrically-opposite flexible tabs 168, but a different number of flexible tabs could be envisaged, e.g. a single tab, or more than two tabs. As can be seen in FIGS. 16 and 17 in particular, while the piston 19 has not ended its axial movement in said dashpot 16, it prevents said flexible tabs 168 of the dashpot 16 from deforming radially inwards. When said piston 19 has ended its axial movement in said dashpot 16, it no longer blocks said flexible tabs 168, which can then deform radially inwards under the effect of the injection spring 8 that pushes the unit formed by said pusher element 17, said piston 19, and said dashpot 16 axially upwards, and as a result of the co-operation between said flexible tabs 168 and the second sloping wall 108 of the body 1. This can be seen in FIG. 14 in particular.

Figure 19:
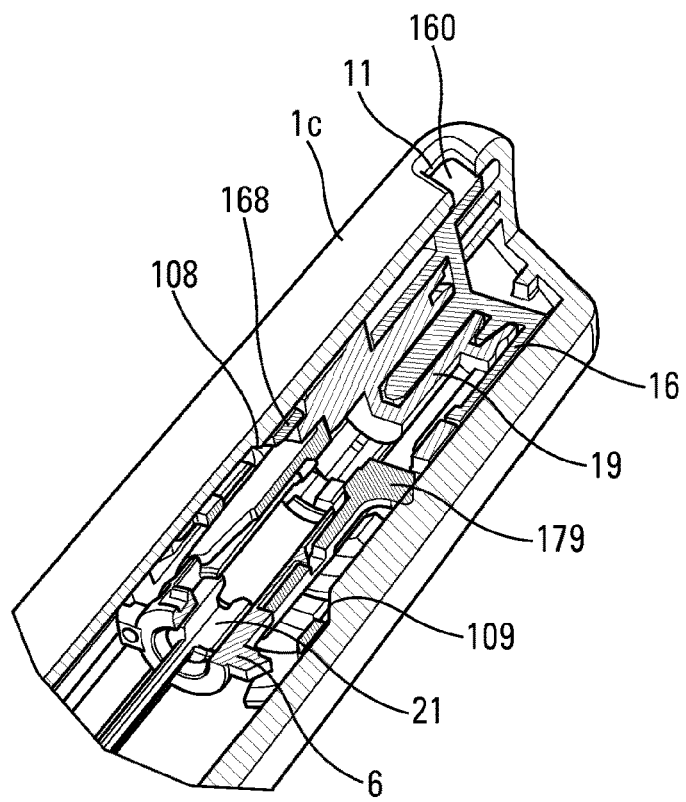
FIG. 19 is a view similar to the views in FIGS. 16 to 18, at the end of actuating the indicator device.

When said piston 19 has ended its axial movement in said dashpot 16, said dashpot is thus released from being blocked, and the unit formed of the pusher element 17, of the piston 19, and of the dashpot 16 is thus projected by the injection spring 8 axially against the end wall of the upper body 1c, as shown in FIG. 19. The indicator portion 160 of the dashpot 16 is thus arranged facing the indication window 11 of the body 1. This non-braked movement or projection of said unit also makes it possible to generate an audible indication by contact between the dashpot 16, the piston 19, and/or the pusher element 17, with the body 1. This audible indication may be made at said indicator portion 160 or on another portion of the unit formed by the pusher element 17, the piston 19, and the dashpot 16, that is adapted to co-operate with an appropriate portion of the body 1. It should be observed that the impact that generates the audible indication may also provide tactile indication by causing the autoinjector to vibrate in the user's hand, which is useful in particular for the hard of hearing.

Figure 27:
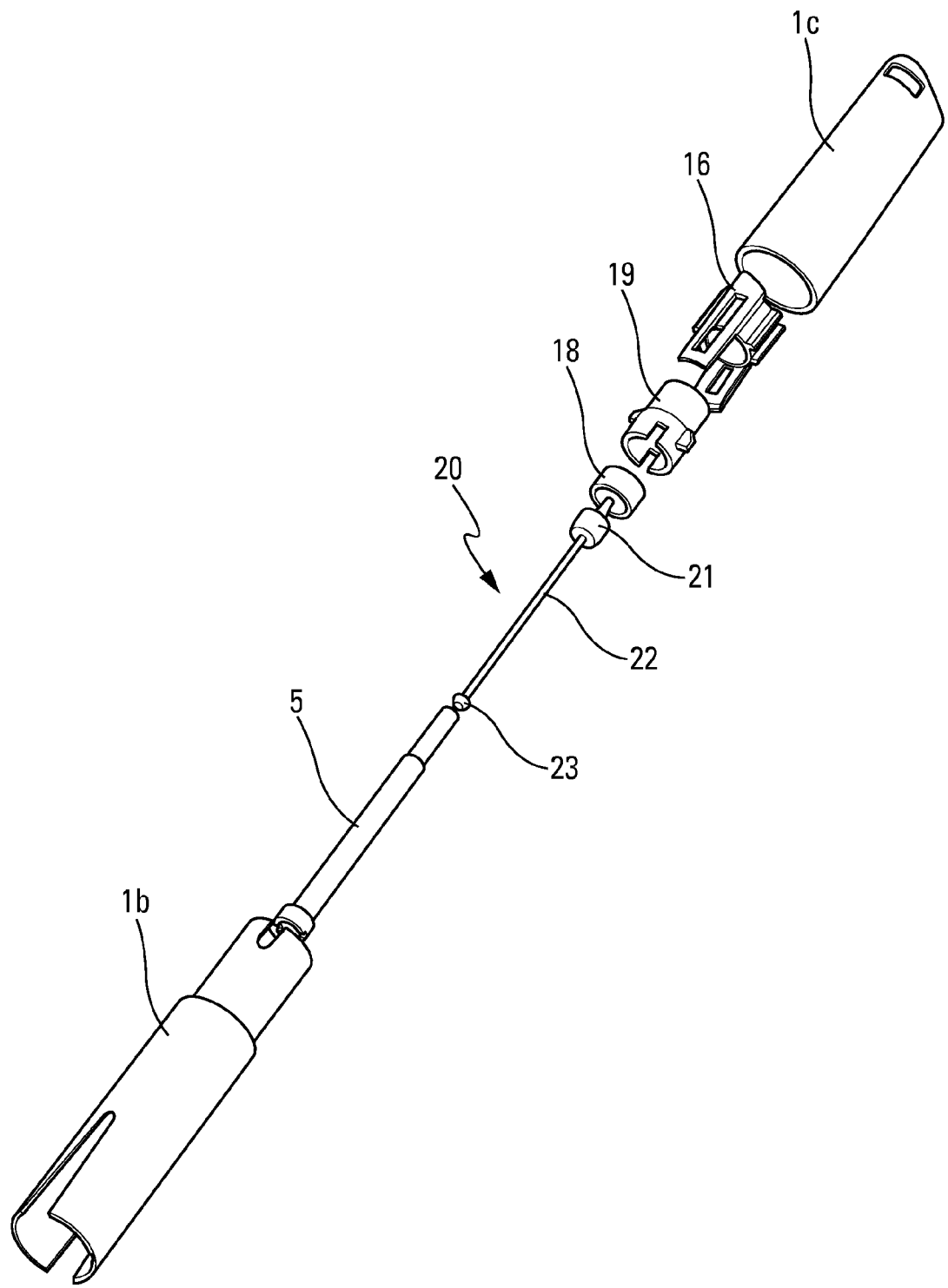
FIG. 27 is an exploded perspective view of the retarding system of said embodiment in FIGS. 20 to 26.
Figure 28:
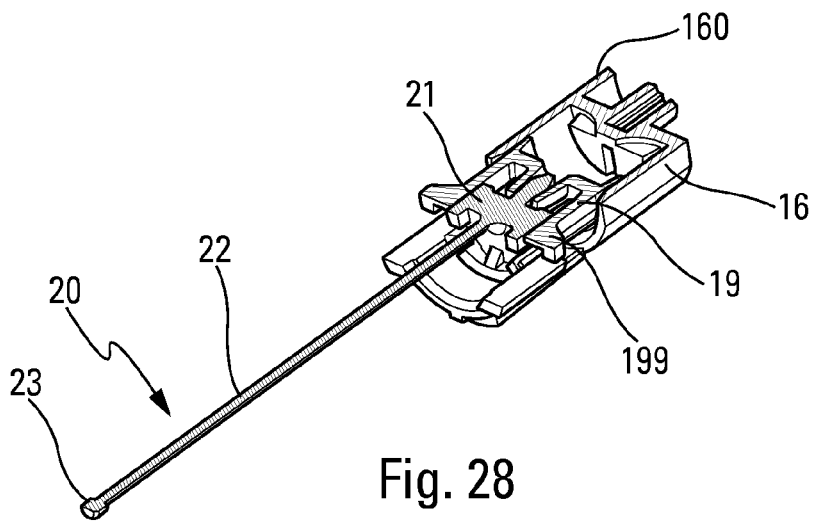
FIGS. 28 to 30 are fragmentary perspective views in section of the FIG. 27 system, showing the sub-assembly formed of the dashpot, the piston, the locking key, and the spring, respectively at the start, during, and at the end of actuation of the retarding system.
Figure 29:
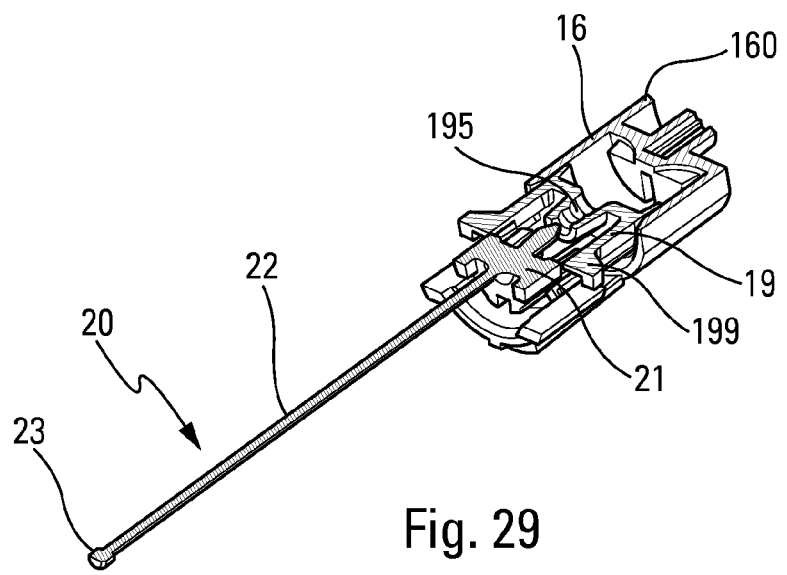
Figure 30:
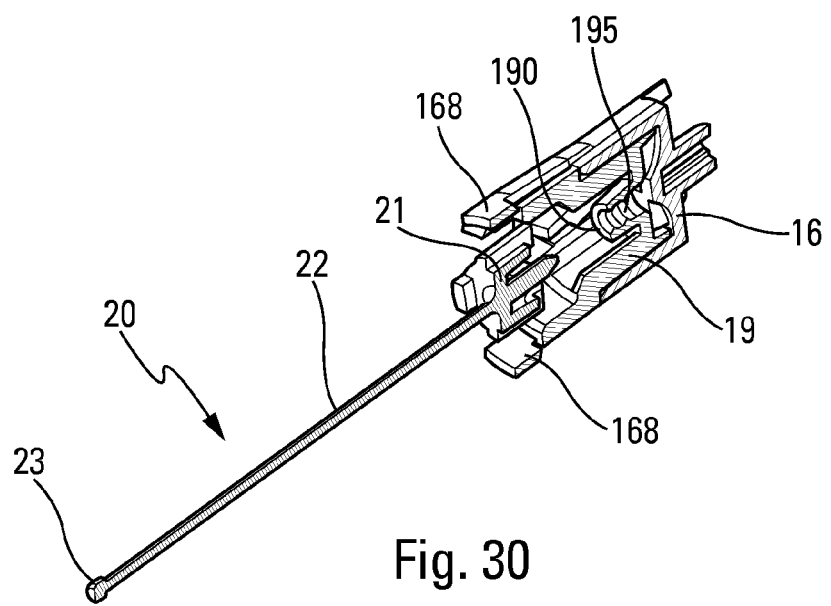

FIG. 27 is an exploded diagrammatic perspective view of the retarding system of another advantageous embodiment. The retarding system comprises the upper body 1c, the dashpot 16 containing an appropriate fluid, the piston 19 arranged in said dashpot 16, a retarding spring 18, a locking key 20, the piston rod 5, and the intermediate body 1b.

In the embodiment shown, the dashpot 16 also forms an indicator element of the visual, audible, and/or tactile indicator device. Advantageously, said dashpot 16 may include an appropriate projection 160 for indicating the end of use of the autoinjector in one or more windows 11 of the body 1, in particular of the upper body 1c. In the embodiment shown in FIGS. 20 to 34, the body 1 includes a single window 11.

The spring 18 bears firstly against the intermediate body 1b, and secondly against the piston 19, as can be seen in FIGS. 31 to 34 in particular. In a variant, said spring could co-operate with the dashpot.

The locking key 20 comprises a head 21 that is adapted to co-operate with the retarding system, a longitudinal rod 22, and an endpiece 23 that is adapted to co-operate with the piston rod 5.

In the position prior to triggering the retarding system, the head 21 of the locking key 20 is in its blocking position in which it co-operates with an axial recess 190 of the piston 19, such that said piston is prevented from moving in translation by said key. When the piston rod 5 comes towards its end-of-injection position, it co-operates with the endpiece 23 of the locking key 20, and thus pulls said locking key axially downwards. As a result, the head 21 of said locking key 20 moves axially out from said recess 190, such that said piston 19 is no longer prevented from moving in translation by said key 20.

The spring 18 urges the piston 19 to move axially in translation towards the rear of said upper body 1c. While the piston 19 is blocked by said locking key 20, the retarding system is thus also blocked.

Figure 31:
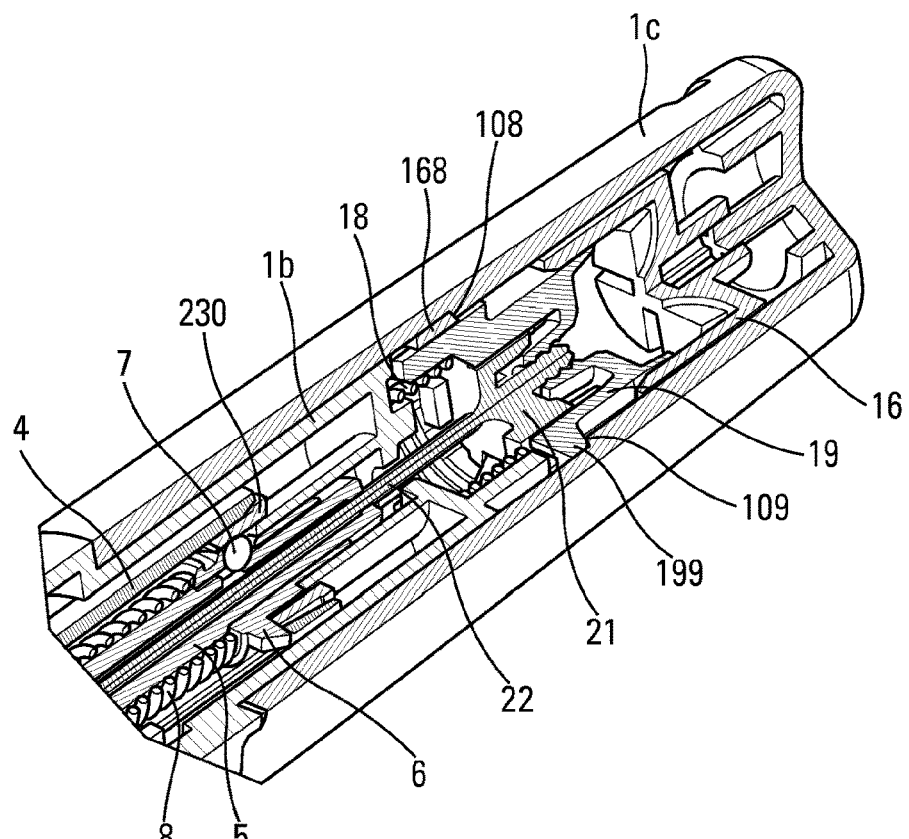
FIGS. 31 to 33 are cut-away perspective views of a detail of the FIG. 27 system, respectively before actuating, after actuating, and at the end of actuating the retarding system.

In the embodiment shown, before actuation of the retarding system, the piston 19 is prevented from performing any axially upward movement by a first frustoconical or sloping wall 109 of the upper body 1c, which wall co-operates with flexible tabs 199 of said piston 19. In the embodiment shown, there are two diametrically-opposite flexible tabs 199, but a different number of first flexible tabs could be envisaged, e.g. a single tab, or more than two tabs. As can be seen in FIG. 31 in particular, in its blocking position, said head 21 of the locking key 20 prevents said flexible tabs 199 of the piston 19 from deforming radially inwards. When said head 21 is no longer in its blocking position, said flexible tabs 199 can deform radially inwards under the effect of the spring 18 that pushes said piston 19 axially upwards, and as a result of the co-operation between said flexible tabs 199 and the first sloping wall 109 of the body 1.

Figure 32:
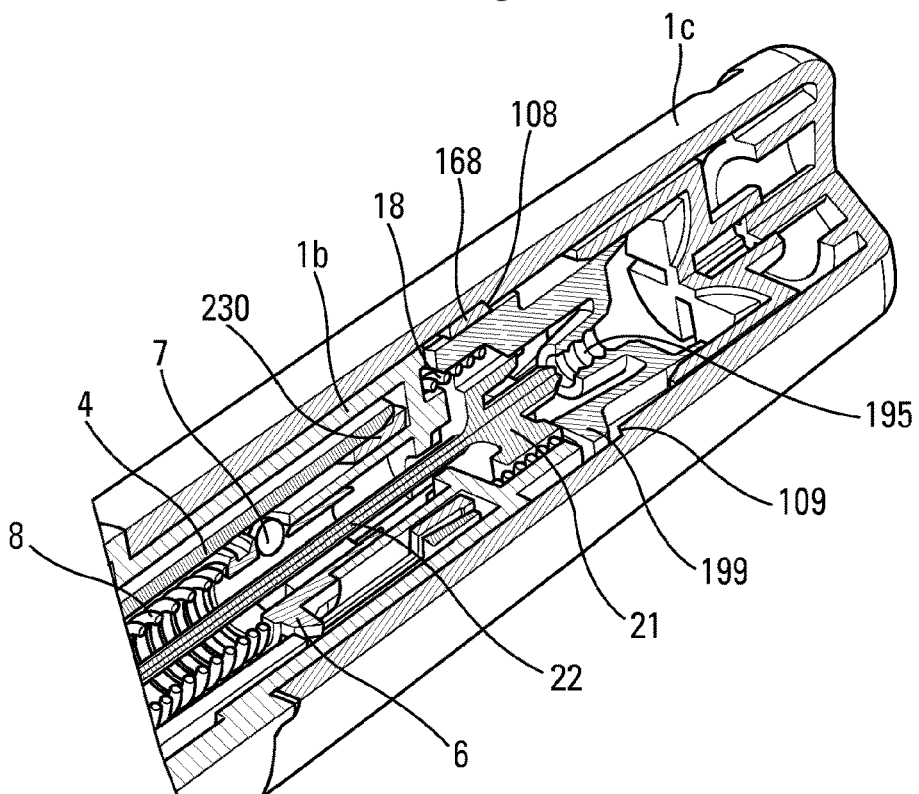
Figure 33:
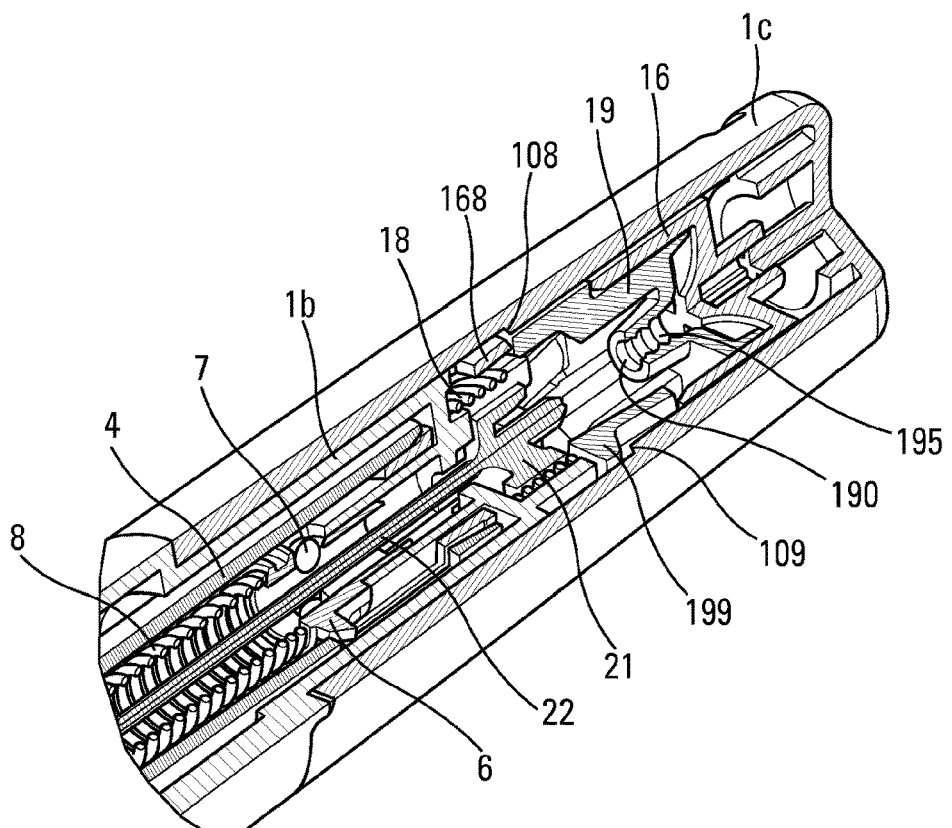

When said locking key 20 releases said piston 19 at the end of injection, said piston is thus moved axially by said spring 18. The retarding system is thus triggered, with said piston 19 moving axially in said dashpot 16. This causes the fluid to be transferred out from said dashpot 16 through one or more appropriate flow passages 195. In the embodiment shown, the flow passage is formed by a central hole in the piston 19, as can be seen in FIGS. 31 to 33 in particular. The central hole axially extends said recess 190 of the piston 19. Advantageously, before actuating the retarding system, the central hole is closed by said head 21 of said locking key 20, thereby makes it possible to seal the dashpot 16. The speed of axial movement of the piston 19 is thus subjected to braking as a result of transferring the fluid out from the dashpot 16 through said flow passage 195.

While said piston 19 is moving in said dashpot 16, said dashpot is prevented from performing any axial movement by flexible tabs 168 of said dashpot 16 that co-operate with a second sloping wall 108 of the body 1, as can be seen in FIGS. 31 and 32. In the embodiment shown, there are two diametrically-opposite flexible tabs 168, but a different number of flexible tabs could be envisaged, e.g. a single tab, or more than two tabs. While the piston 19 has not ended its axial movement in said dashpot 16, it prevents said flexible tabs 168 of the dashpot 16 from deforming radially inwards. When said piston 19 has ended its axial movement in said dashpot 16, it no longer blocks said flexible tabs 168, which can then deform radially inwards under the effect of the spring 18 that pushes the unit formed by said piston 19 and said dashpot 16 axially upwards, and as a result of the co-operation between said flexible tabs 168 and the second sloping wall 108 of the body 1. This can be seen in FIG. 34 in particular.

Figure 34:
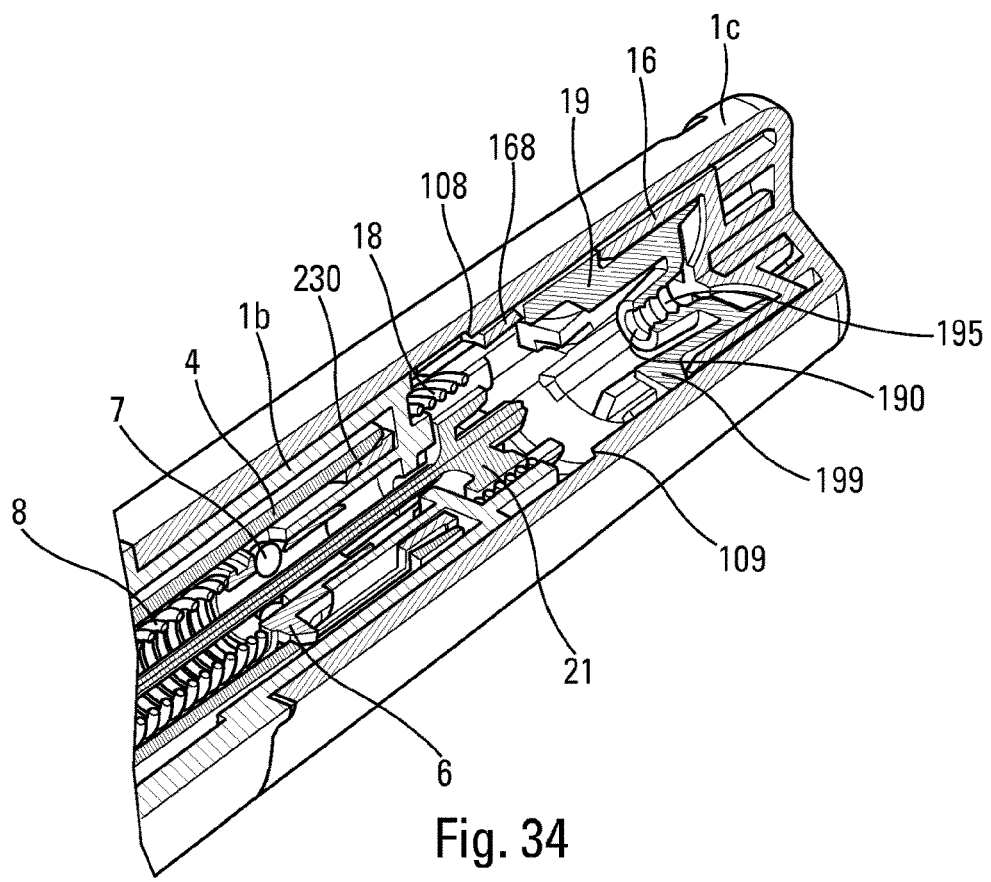
FIG. 34 is a view similar to the views in FIGS. 31 to 33, at the end of actuating the indicator device.

When said piston 19 has ended its axial movement in said dashpot 16, said dashpot is thus released from being blocked, and the unit formed of the piston 19 and of the dashpot 16 is thus projected by the spring 18 axially against the end wall of the upper body 1c, as shown in FIG. 34. The indicator portion 160 of the dashpot 16 is thus arranged facing the indication window 11 of the body 1. This non-braked movement or projection of said unit also makes it possible to generate an audible indication by contact between the dashpot 16 and/or the piston 19, with the body 1. This audible indication may be made at said indicator portion 160 or on another portion of the unit formed by the piston 19 and the dashpot 16, that is adapted to co-operate with an appropriate portion of the body 1. It should be observed that the impact that generates the audible indication may also provide tactile indication by causing the autoinjector to vibrate in the user's hand, which is useful in particular for the hard of hearing.

In both of the embodiments described above, the fluid used in the retarding system may be of any appropriate type, e.g. grease. The use of a fluid having viscoelastic properties is advantageous.

The retarding device thus makes it possible to offset, by a predetermined time, the moment at which the indicator indicates the end of use, from the moment at which the injection stage has ended.

A complete actuation stage of the autoinjector is described below.

When the user wishes to use the autoinjector, the user takes hold of the device, e.g. at the body 1, and presses the actuator sleeve 10, which at rest, in its first projecting position, projects out from the lower body 1, against the part of the body where the injection is to be performed. In FIG. 1a, 1b and 2a, 2b firstly, and 20a, 20b and 21a, 21b secondly, it can be seen that the pressure exerted by the user on the actuator sleeve 10 causes said actuator sleeve to slide inside the body 1, thereby uncovering the needle and thus pricking the user as a result of the pressure exerted by the user on the autoinjector.

When the actuator sleeve 10 reaches its actuated position, which is its end position inside the body 1, it causes the injection stage to be triggered, which is shown in FIGS. 3a, 3b and 4a, 4b firstly, and 22a, 22b and 23a, 23b secondly. It should be observed that the piston rod 5 slides inside the syringe A, pushing the piston P of said syringe under the effect of the injection spring 8. The fluid is thus dispensed.

At the end of injection, the retarding system is triggered, such that the indicator device is actuated only after a predetermined time delay.

After indicating the end of use, when the user removes the autoinjector from the injection site, the actuator sleeve 10 once again moves out from the body 1 towards the end-of-use position, which is its second projecting position, under the effect of the spring of the actuator sleeve, with said actuator sleeve 10 being locked, and this guarantees absolute safety for the user and avoids any risk of injury with the needle after the device has been used.

In the embodiment shown, the first and second projecting positions of the actuator sleeve are different positions, however it should be observed that they could optionally be identical.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to an advantageous embodiment, naturally said embodiment is not limiting. In particular, the actuator sleeve and/or the injection lock and/or the retarding device and/or the audible and/or tactile indicator device could be made in some other way. Pricking by the needle and/or retracting the needle after injection could be controlled by one or more buttons. Other modifications can also be envisaged by the person skilled in the art, without going beyond the ambit of the present invention, as defined by the accompanying claims.

The invention claimed is:

1. An autoinjector comprising:
a body receiving a reservoir, said reservoir containing fluid and including a piston, such as a pre-filled syringe;
a piston rod that is adapted to co-operate with the piston of said reservoir, said piston rod being movable by an injection spring between a primed position and an injection position in which said piston rod has moved the piston of the reservoir so as to inject the fluid into an injection site; and
a visual, audible, and/or tactile indicator device for indicating to the user that said autoinjector may be removed from said injection site;
said autoinjector being characterized in that it includes a retarding system for delaying the actuation of said visual, audible and/or tactile indicator device relative to the end of injection, said retarding system including a dashpot containing a fluid, a piston being arranged in said dashpot, one of said dashpot and of said piston being movable in translation in said body during actuation of said retarding system, and the other of said dashpot and of said piston being stationary relative to said body during actuation of said retarding system, the movement in translation of one relative to the other moving said fluid out from said dashpot through at least one flow passage, such that said movement in translation is braked, said retarding system comprising said dashpot containing said fluid, said piston, a locking key, said injection spring, a pusher element, a support member interposed between said pusher element and said injection spring, and said piston rod, said locking key comprising a head, a longitudinal rod, and an endpiece that is adapted to co-operate with the piston rod, said head of the locking key being in its blocking position before triggering the retarding system, in which position it co-operates with a recess of said pusher element, said piston rod, when it arrives towards its end-of-injection position, co-operating with the endpiece of the locking key so as to pull said locking key axially downwards out from its blocking position, such that said pusher element is thus no longer prevented from moving in translation by said locking key.

2. The autoinjector according to claim 1, wherein, during actuation of said retarding system, said piston is movable in translation in said body, and said dashpot is stationary.

3. The autoinjector according to claim 2, wherein, during actuation of said retarding system, said dashpot is prevented from moving in translation by a frustoconical or sloping wall portion of said body that co-operates with at least one flexible tab of said dashpot, said piston, during actuation of said retarding system, preventing said flexible tabs from deforming radially inwards.

4. The autoinjector according to claim 3, wherein, after actuating said retarding system, said piston is moved axially relative to said at least one flexible tab of said dashpot and no longer prevents it from deforming radially inwards, such that said dashpot is no longer prevented from moving in translation in said body.

5. The autoinjector according to claim 1, wherein said at least one flow passage is formed by an axial groove in the dashpot.

6. The autoinjector according to claim 1, wherein said at least one flow passage is formed by a central hole in the piston.

7. The autoinjector according to claim 1, wherein said pusher element is axially movable in said body and co-operates with said piston, such that an axial movement of said pusher element causes an axial movement of said piston in said dashpot.

8. The autoinjector according to claim 1, wherein said pusher element includes flexible tabs that, before actuation of the retarding system, co-operate with a frustoconical or sloping wall of the body, the head of the locking key, in its blocking position, preventing said flexible tabs from deforming radially inwards.

9. The autoinjector according to claim 1, wherein said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

10. The autoinjector according to claim 1, wherein said reservoir includes a needle through which said fluid is injected into said injection site.

* * * * *